United States Patent
Nehdi et al.

(10) Patent No.: US 11,052,101 B2
(45) Date of Patent: Jul. 6, 2021

(54) METHODS FOR TREATING CANCER USING PURINE ANALOGS BY DEPLETING INTRACELLULAR ATP

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventors: Atef Nehdi, Riyadh (SA); Mohamed Boudjelal, Riyadh (SA); Ahmed Alaskar, Riyadh (SA)

(73) Assignees: National Guard Health Affairs, Riyadh (SA); King Saud bin Abdulaziz University for Health Sciences, Riyadh (SA); King Abdullah International Medical Research Center, Riyadh (SA)

(*) Notice: Subject to any disclaimer, the term of this patent is extended or adjusted under 35 U.S.C. 154(b) by 0 days.

(21) Appl. No.: 16/585,705

(22) Filed: Sep. 27, 2019

(65) Prior Publication Data
US 2020/0306285 A1     Oct. 1, 2020

Related U.S. Application Data

(60) Provisional application No. 62/823,311, filed on Mar. 25, 2019.

(51) Int. Cl.
| | | |
|---|---|---|
| *A01N 43/04* | (2006.01) | |
| *A61K 31/70* | (2006.01) | |
| *A61K 31/7076* | (2006.01) | |
| *A61P 35/02* | (2006.01) | |
| *A61K 31/519* | (2006.01) | |
| *A61K 31/137* | (2006.01) | |

(52) U.S. Cl.
CPC ........ *A61K 31/7076* (2013.01); *A61K 31/137* (2013.01); *A61K 31/519* (2013.01); *A61P 35/02* (2018.01)

(58) Field of Classification Search
None
See application file for complete search history.

(56) References Cited

U.S. PATENT DOCUMENTS

| | | |
|---|---|---|
| 2003/0018014 A1 | 1/2003 | Lerner |
| 2011/0097337 A1 | 4/2011 | Preville et al. |
| 2011/0151020 A1 | 6/2011 | Heeschen et al. |
| 2016/0122406 A1 | 5/2016 | Coy et al. |

FOREIGN PATENT DOCUMENTS

| | | |
|---|---|---|
| EP | 1 289 557 B1 | 7/2006 |

OTHER PUBLICATIONS

Kano et al. Leukemia (2000), vol. 14, pp. 379-388.*
Jensen, et al.; Cytotoxic purine nucleoside analogues bind to A1, A2A, and A3 adenosine receptors; Archiv für Experimentelle Pathologie und Pharmakologie; Jan. 2012; 8 Pages.
McEwan, et al.; Chemoresistant KM12C Colon Cancer Cells Are Addicted to Low Cyclic AMP Levels in a Phosphodiesterase 4-Regulated Compartment via Effects on Phosphoinositide 3-Kinase; Cancer Research; Jul. 2007; 12 Pages.

* cited by examiner

*Primary Examiner* — Patrick T Lewis
(74) *Attorney, Agent, or Firm* — Oblon, McClelland, Maier & Neustadt, L.L.P.

(57) ABSTRACT

The invention is directed to a method for treating a cancer patient by administering an agent that depletes intracellular ATP along with a purine analog, such as fludarabine. It is also directed to a method for selecting a patient having cancer cells susceptible to depletion of their intracellular ATP.

20 Claims, 28 Drawing Sheets

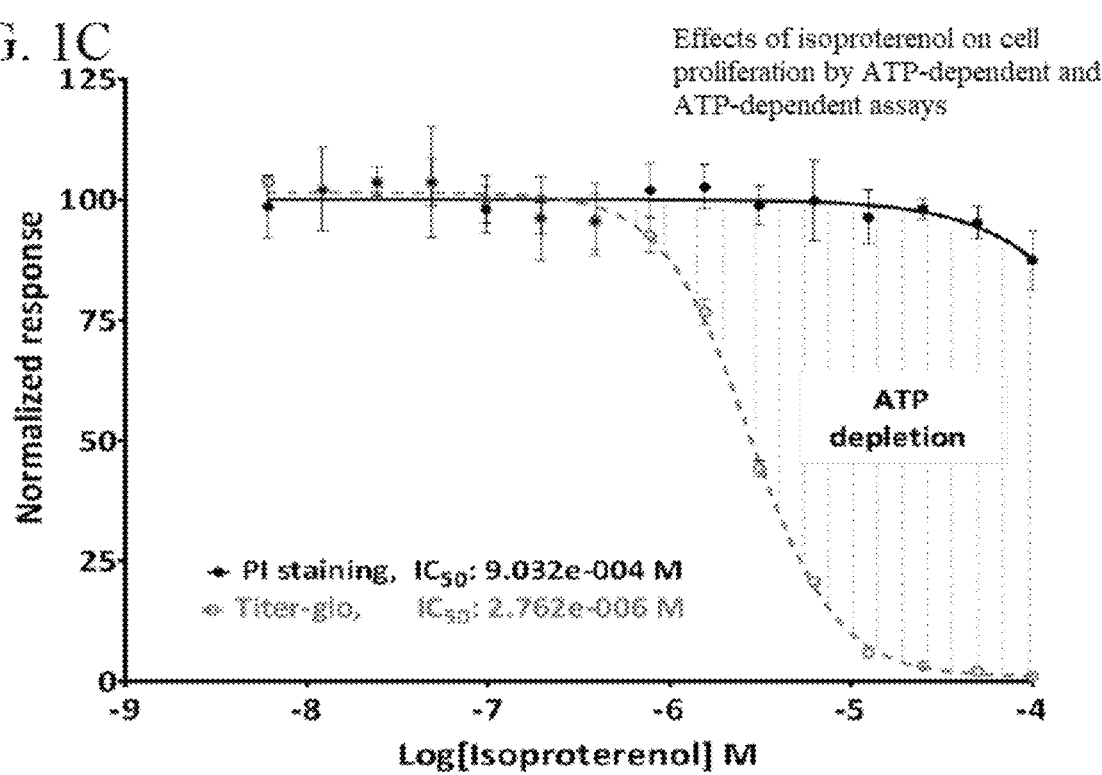

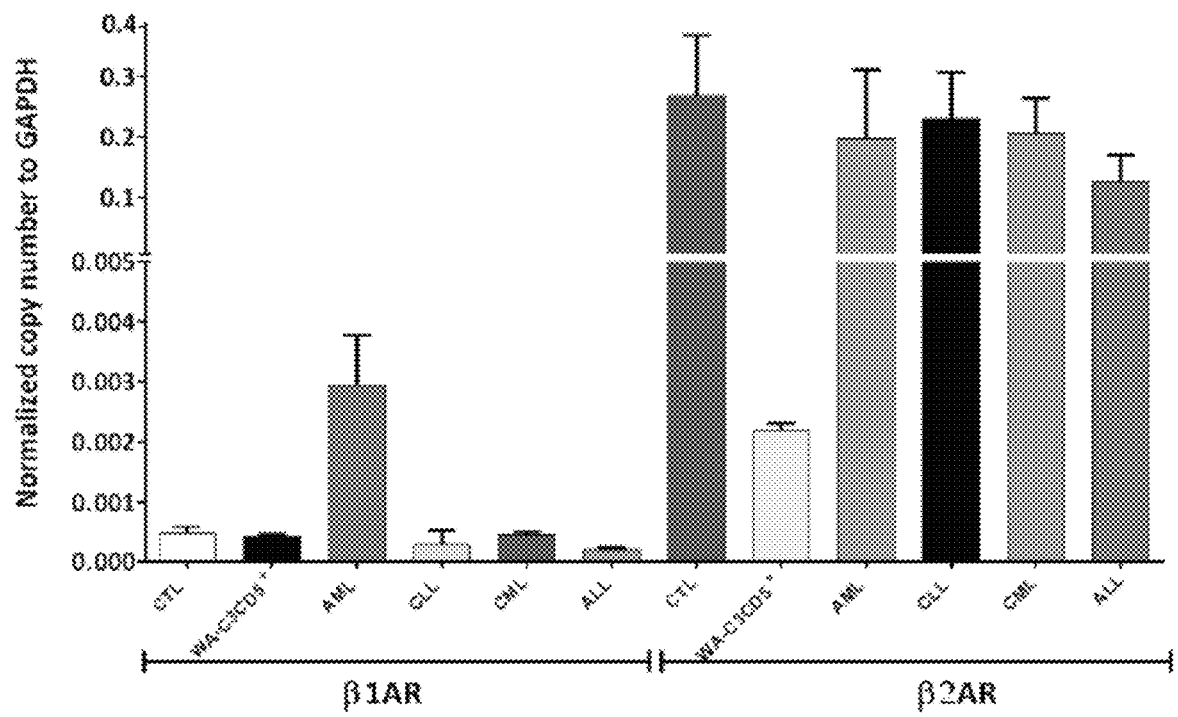

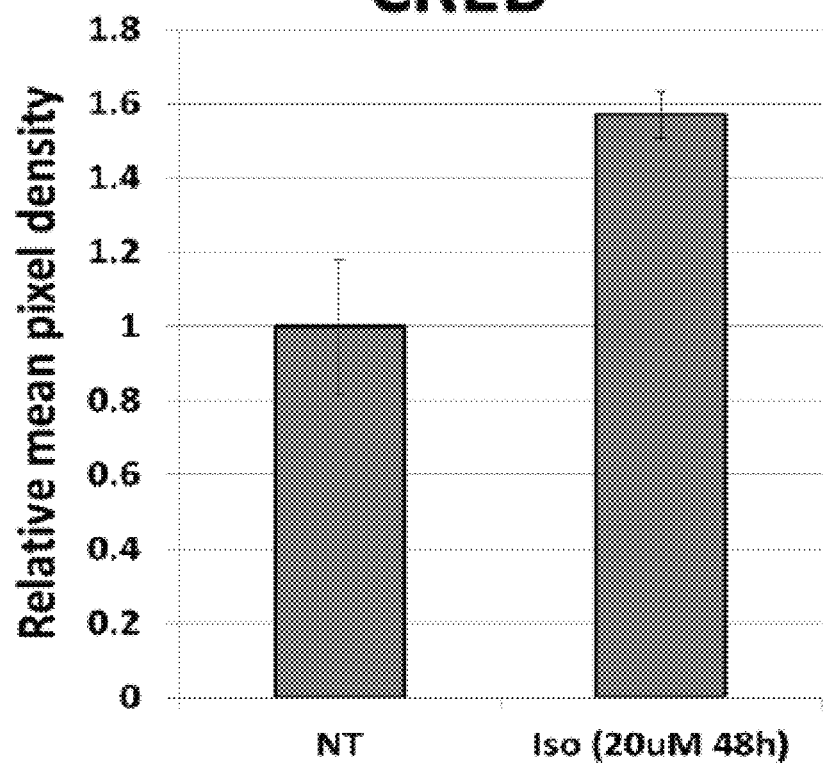

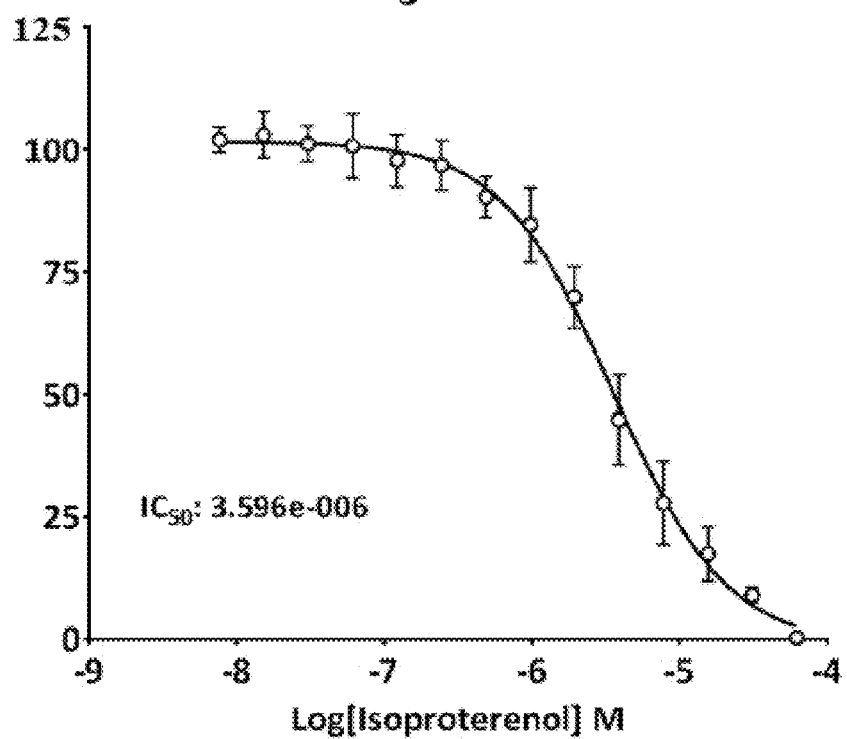
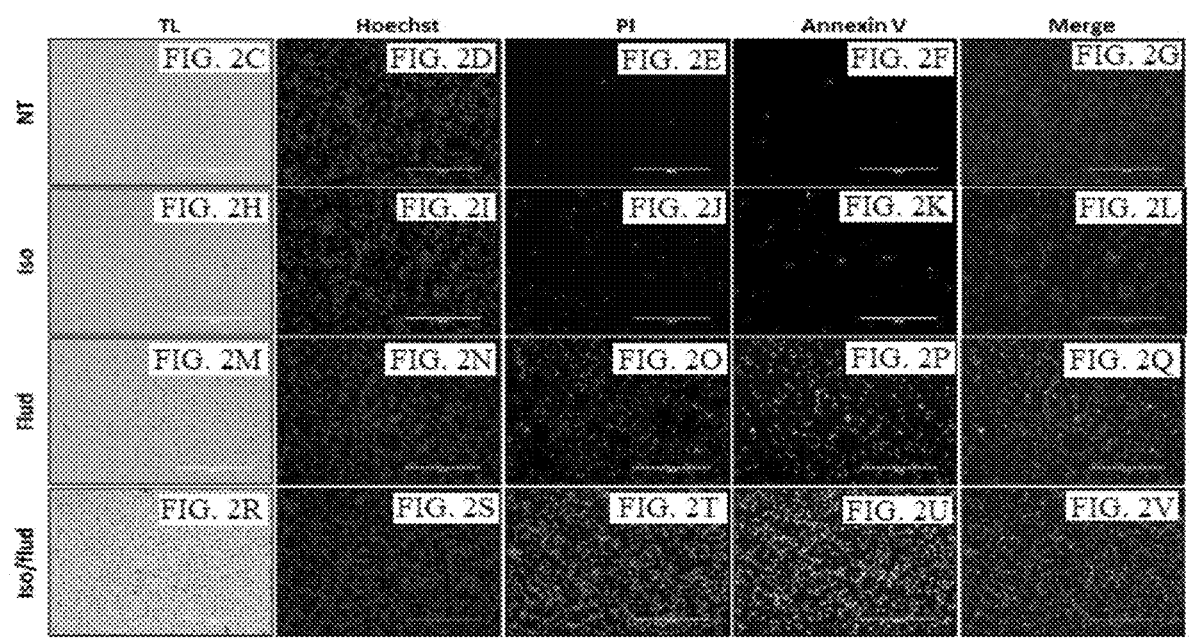

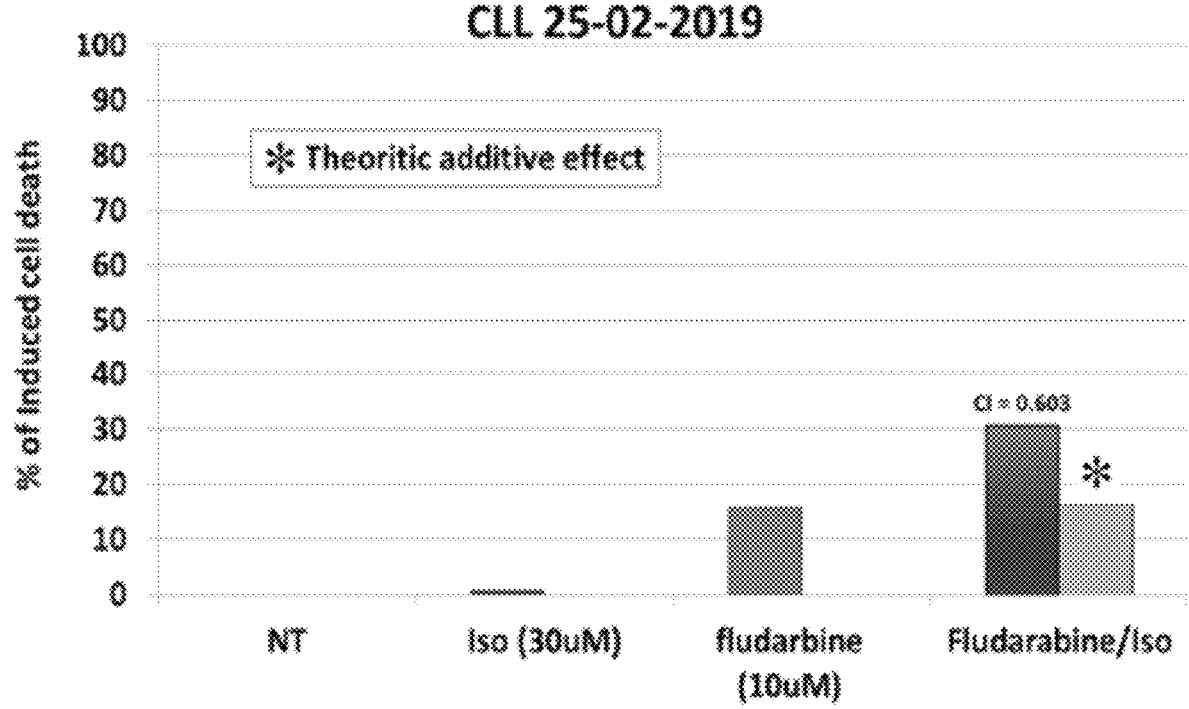

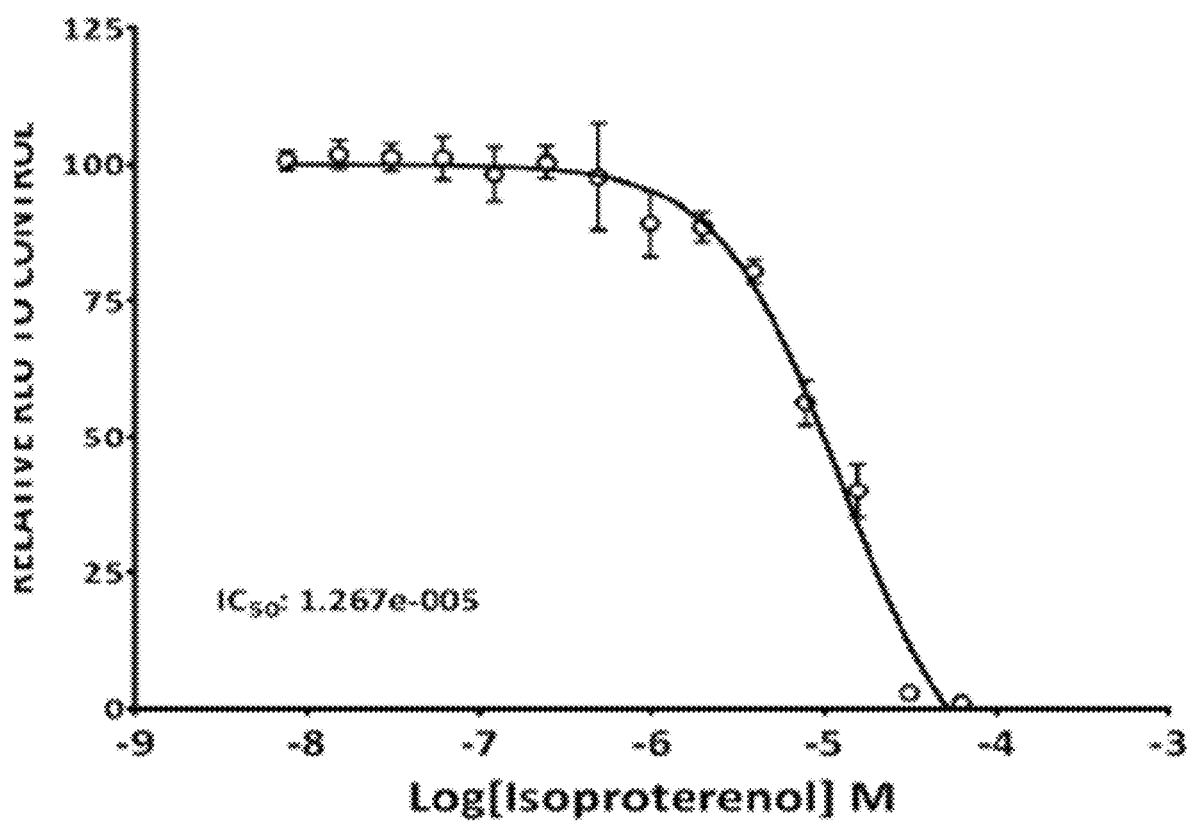

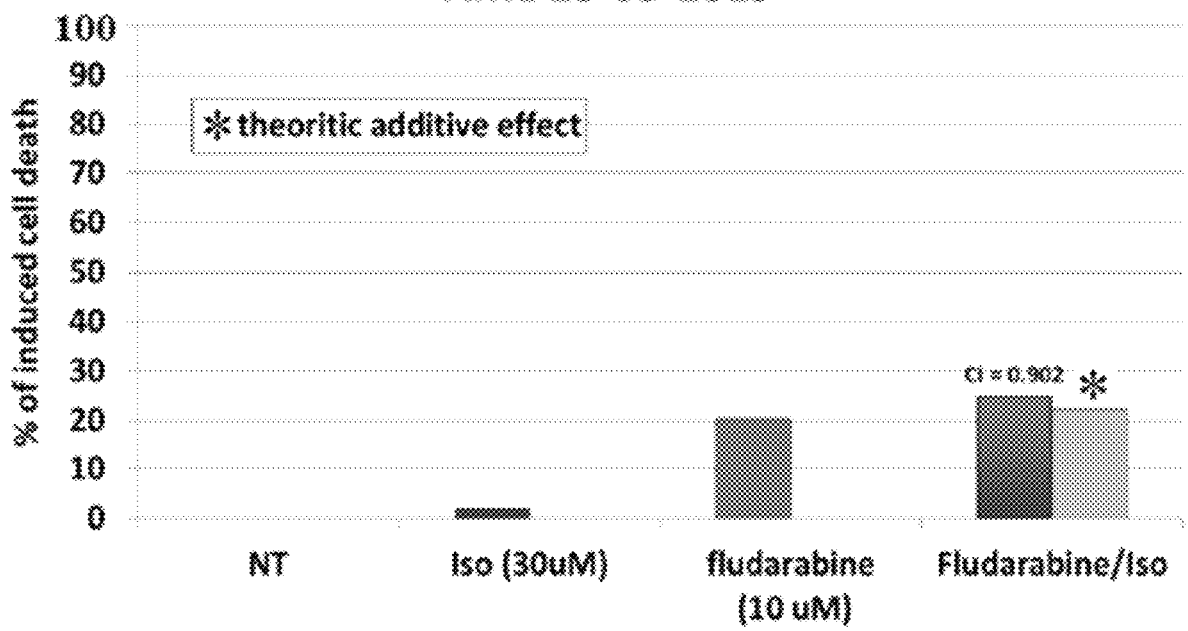

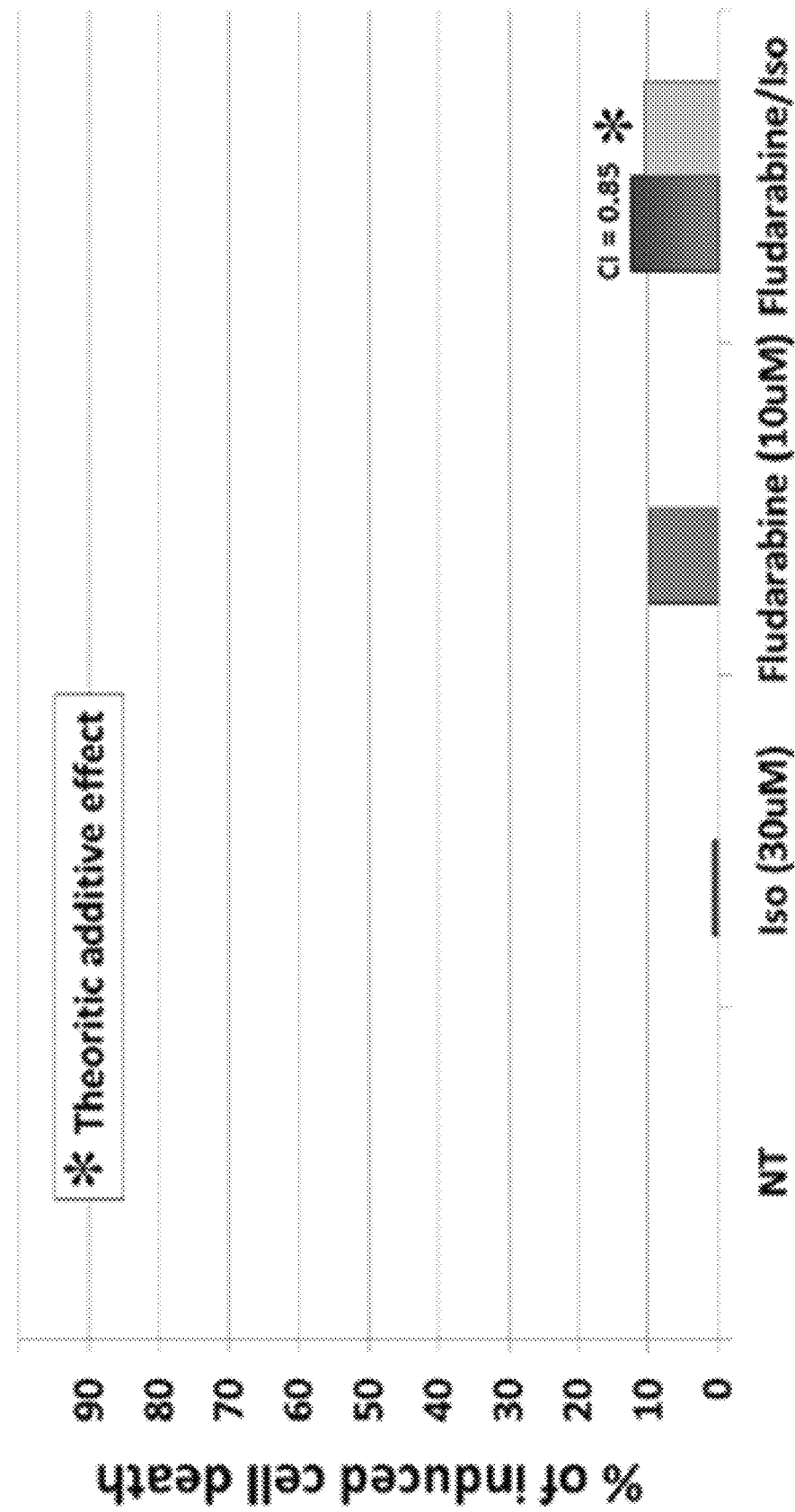

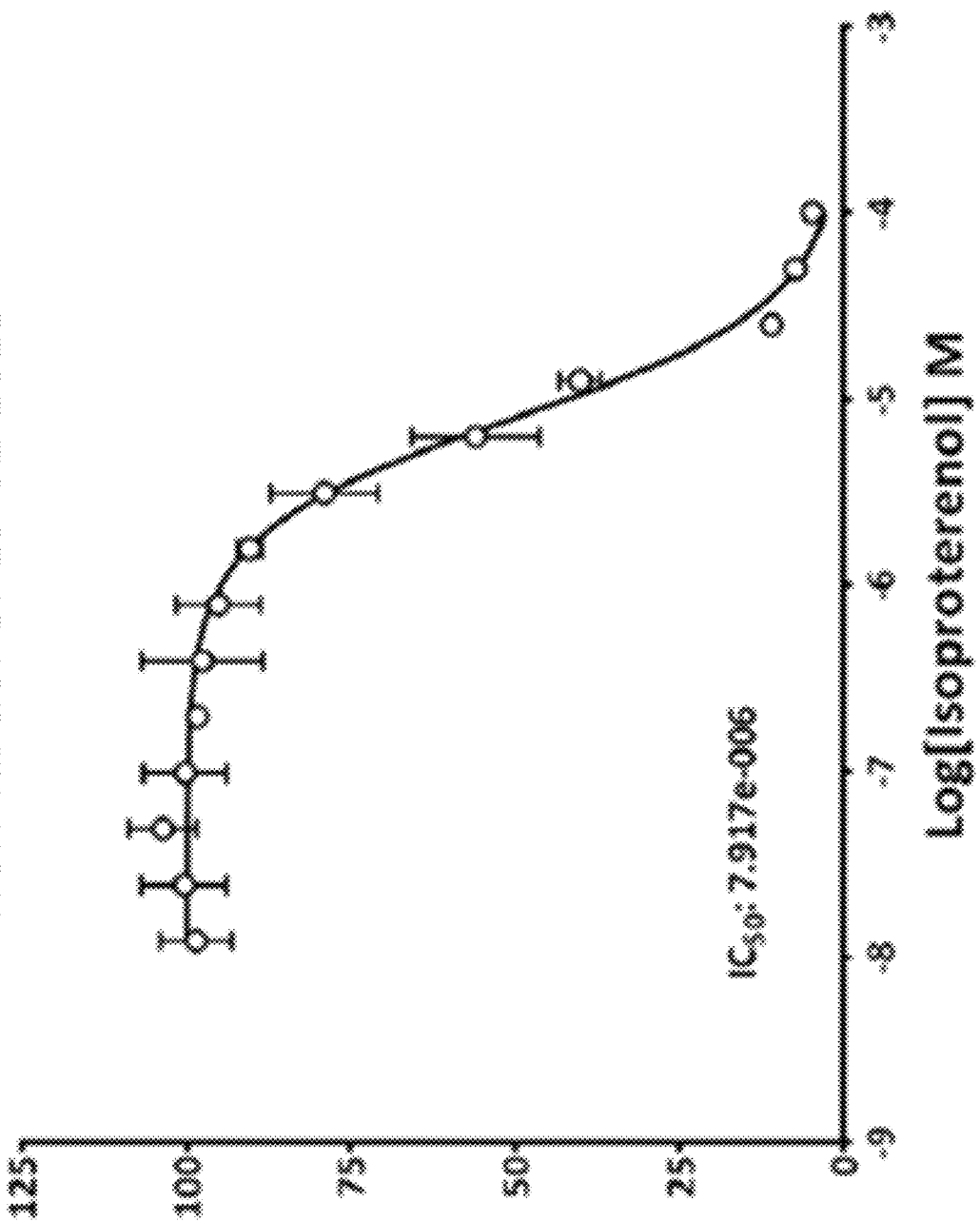

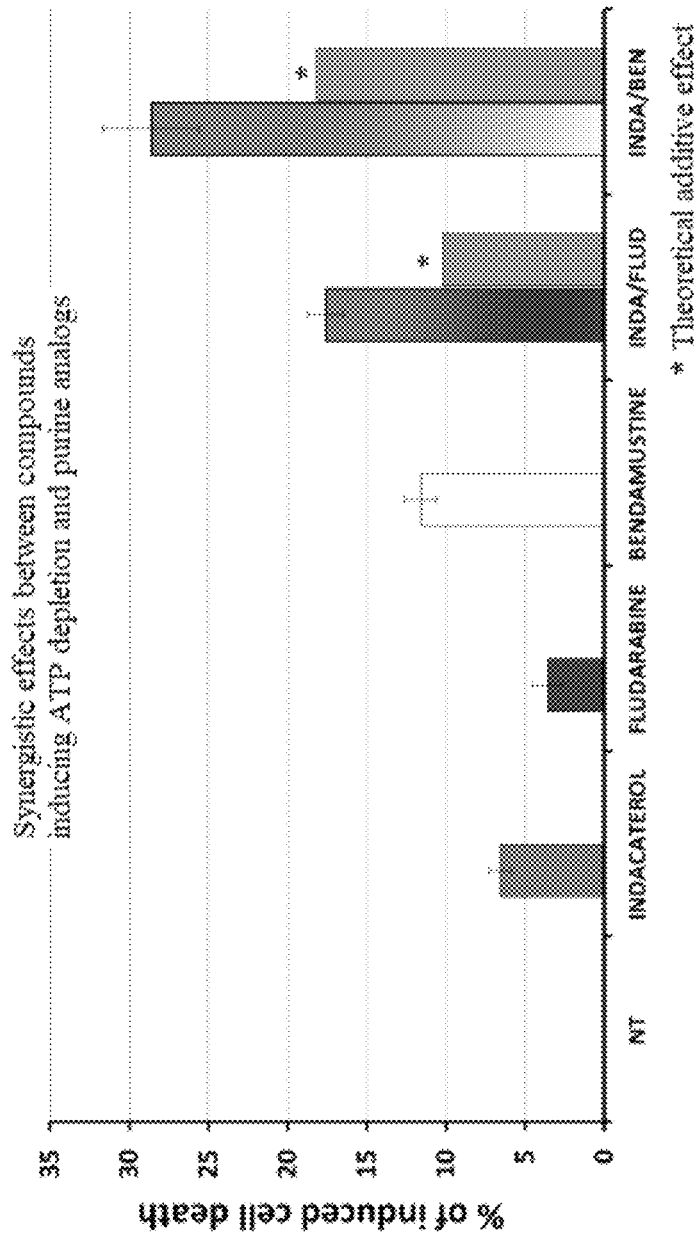

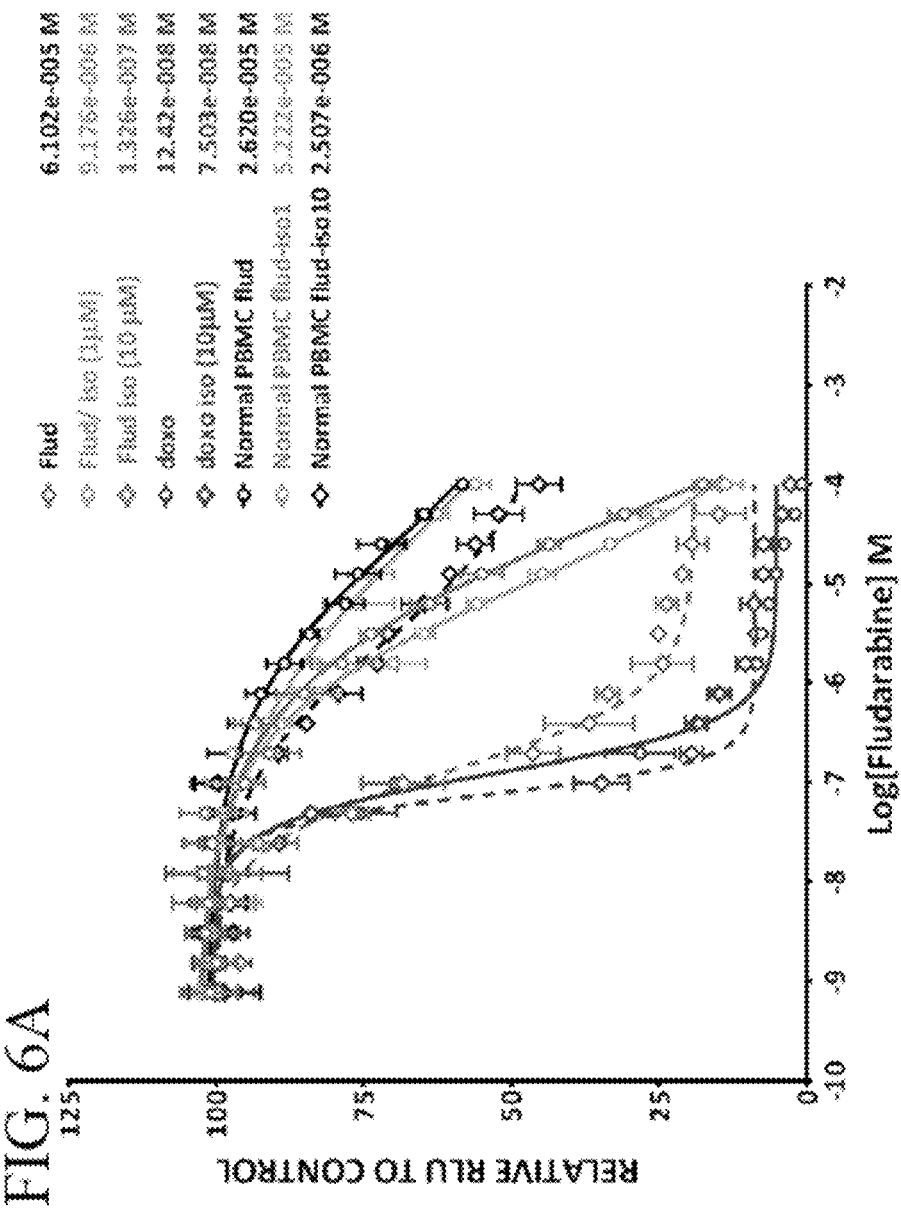

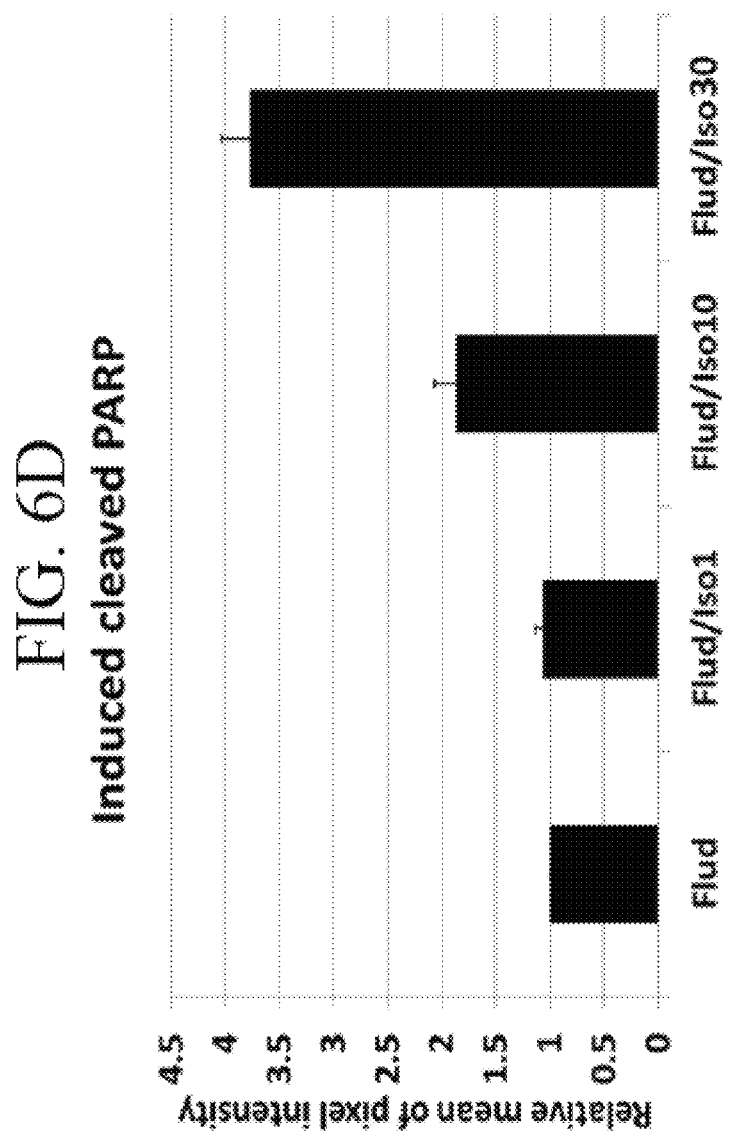

FIG. 8
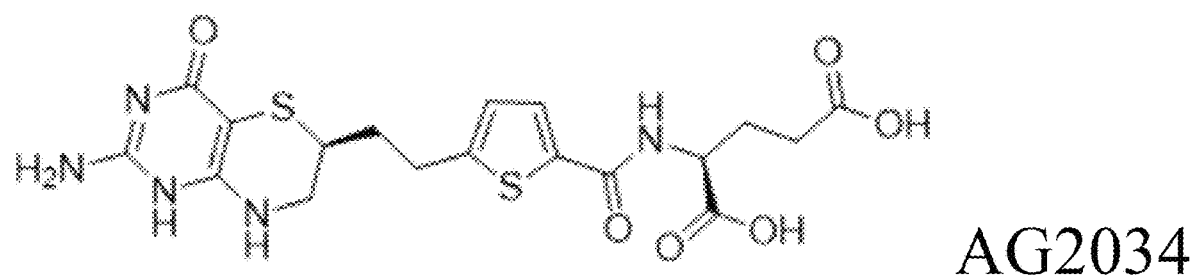 AG2034
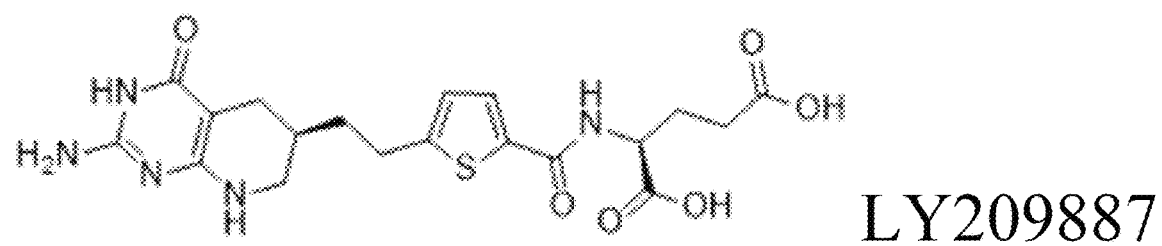 LY209887
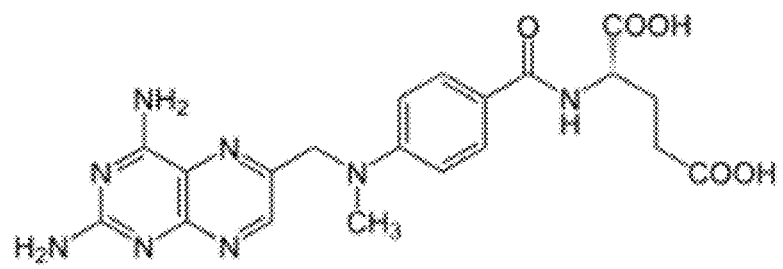
Methotrexate

METHODS FOR TREATING CANCER USING PURINE ANALOGS BY DEPLETING INTRACELLULAR ATP

CROSS-REFERENCE TO RELATED APPLICATIONS

This application claims priority to U.S. Provisional Application No. 62/823,311, filed Mar. 25, 2019 which is hereby incorporated by reference for all purposes.

BACKGROUND OF THE INVENTION

Field of the Invention

The invention falls within the field of oncology and more generally medicine.

Description of Related Art

Isoproterenol (isoprenaline; CAS Registry Number: 7683-59-2, "Iso"), is a medication used for the treatment of bradycardia (slow heart rate), heart block, and rarely for asthma. It is a non-selective β adrenoreceptor agonist that is the isopropylamine analog of epinephrine (adrenaline). Other uses include treatment of certain types of abnormal heartbeats, heart failure (weak heart) or shock.

Fludarabine (CAS Registry Number: 21679-14-1, "Flud"), sold under the brand name Fludara® among others, is a purine nucleoside analog and a chemotherapy medication used in the treatment of leukemia and lymphoma. These include chronic lymphocytic leukemia, non-Hodgkin's lymphoma, acute myeloid leukemia, and acute lymphocytic leukemia. It is a first line drug for patients with chronic lymphocytic leukemia. It is given by injection into a vein or by mouth. Unfortunately, after treatment with fludarabine a population of fludarabine-resistant cells cancer cells appears. Thus patients treated with fludarabine often have a low rate of complete remission and the development of fludarabine-resistance is one of the predominant reasons for treatment failure with fludarabine. Fludarabine resistance has been studied but practical ways to employ this research to treat patients with fludarabine-resistant cancers is lacking; Pandzci, et al., Clin Cancer Res. 2016 Dec. 15; 22(24):6217-6227. Epub 2016 Mar. 8; Moussey, et al., Mol Cancer. 2010 May 20; 9:115. doi: 10.1186/1476-4598-9-115.

Ways to side-step development of fludarabine resistance or to significantly boost efficacy of fludarabine are needed especially in patients developing fludarabine resistant cancer cells and in those where fludarabine is the only practical choice. With these objectives in mind the inventors sought to determine whether efficacy of fludarabine treatment could be enhanced by combination with other drugs, such as with isoproterenol which deplete intracellular ATP.

The background description provided herein is for the purpose of generally presenting the context of the disclosure. All references cited herein are incorporated by reference. Work of the presently named inventors, to the extent it is described in this background section, as well as aspects of the description which may not otherwise qualify as prior art at the time of filing, are neither expressly or impliedly admitted as prior art against the present disclosure.

BRIEF SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawings.

The inventors have found that concurrent use of isoproterenol and other compounds depleting intracellular ATP will sensitize cancer cells to fludarabine providing a way to eradicate otherwise fludarabine-resistant cells. Intracellular ATP and fludarabine, which is a purine nucleotide analog, compete for the binding to common enzymes inside the cancer cell (e.g., enzymes required in DNA synthesis such as ribonucleotide reductase, DNA primase, DNA polymerases, 3'-5' exonuclease activity of DNA polymerases delta and epsilon, and DNA ligase I) and depletion of intracellular ATP permits enhanced binding of fludarabine to target proteins in cancer cells thus providing superior and/or synergistic cytotoxic effects. Treatment methods disclosed herein require the administration of both a purine analog and a compound that reduces ATP levels. ATP competes with the purine analog for cancer cell ATP-binding enzymes, thus reducing the level of ATP increases the relative affinity of the purine analog to its target enzymes in the cancer cell and increases the efficacy of treating the cancer.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings below.

FIG. 1C. Cytotoxic effect induced by a gradient of isoproterenol concentrations (dose-response) was assessed with an ATP-dependent (cell-titer Glo®, dashed line) and ATP-independent assay (MTT).

FIG. 1D. The level of expression of the different adrenergic receptors in primary leukemic cells (ALL, AML, CLL and CML), normal PBMCs and in the CLL cell line WA-C3CD5+ as measured by quantitative real time PCR (qPCR).

FIG. 1G. Relative levels of protein phosphorylation (normalized intensity for each antibody) were calculated for each untreated and treated sample. p-CREB (indicated by black arrow) was the only significantly up-regulated kinase upon Iso treatment.

FIG. 2B. Average of Isoproterenol-induced intracellular ATP depletion in primary CLL cells used in FIG. 2A. Intracellular ATP was measured by the ATP-based luminescent assay CellTiter-Glo®.

FIGS. 2C-2V. Annexin V/PI staining of CLL primary cells treated with fludarabine alone or in combination with Isoproterenol.

FIGS. 3A-3B: Graphs depicting % induced cell death due to treatment with Iso (30 uM), fludarabine (10 uM) or their combination. FIG. 3B shows Iso-induced intracellular ATP depletion in primary CLL cells isolated from a CLL patient at early stage.

FIGS. 3C-3D. Graphs depicting % induced cell death due to treatment with Iso (30 uM), fludarabine (10 uM) or their combination. FIG. 3D shows Iso-induced intracellular ATP depletion in primary AML cells isolated from an AML patient at early stage.

FIGS. 3E and 3F. Graphs depicting % induced cell death due to treatment with Iso (30 uM), fludarabine (10 uM) or their combination. FIG. 3F shows Iso-induced intracellular ATP depletion in cells from a normal patient.

FIG. 4. Bar graph depicting increase in induced cell death between various ATP depleting agents and purine analogs.

FIGS. 6A-6C shown that isoproterenol synergizes specifically with the purine analogue fludarabine in dose-dependent manner.

FIG. 6A. Results of luminescent-based assay Cell-Titer Glo showing that higher concentrations of isoproterenol increase cytotoxic effects of fludarabine and other purine analogs.

FIGS. 6B-6C. Western blots of apoptosis markers in normal and drug-treated cells.

FIG. 6D. Bar graph comparing relative level of apoptosis marker: cleaved PARP in treated cells.

FIG. 8 shows the structures of purine analogs AG2034, LY309887 and methotrexate.

DETAILED DESCRIPTION OF THE INVENTION

Figure 1A:
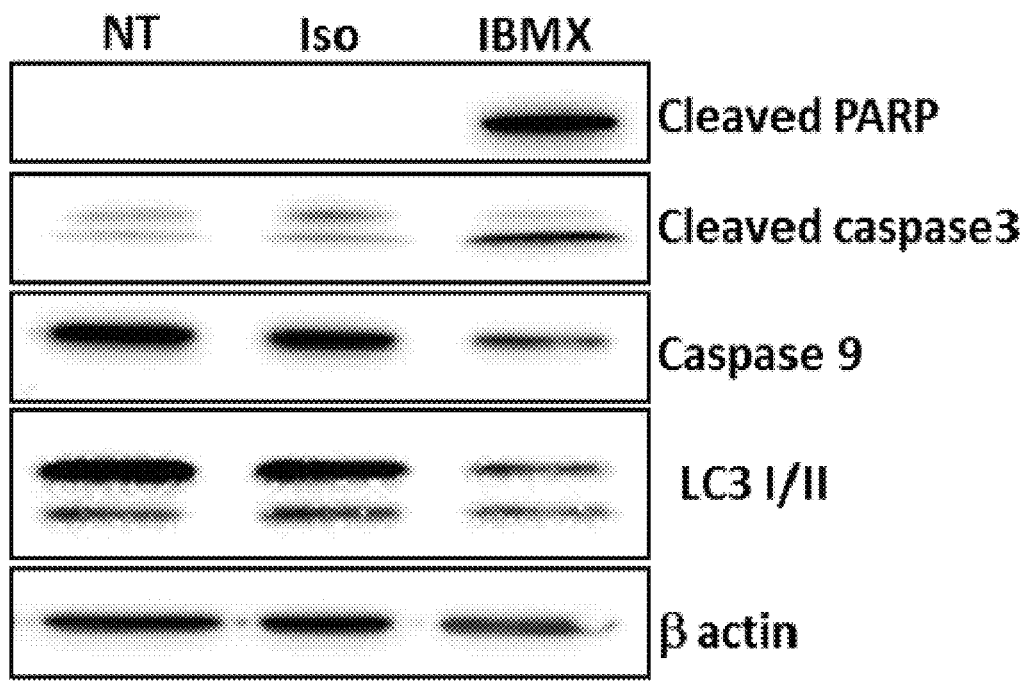
FIG. 1A. Western blot of apoptosis markers from primary CLL cells treated with 3 uM isoproterenol. IBMX was used as a positive control because it induces apoptosis in CLL B cells.

Embodiments of the invention include, but are not limited to the following.

One embodiment of the invention is directed to a method for treating a patient with cancer or other disease, disorder or condition that can be treated with a purine analog comprising administering a purine analog in combination with an agent that depletes intracellular ATP. Preferably, the purine analog is fludarabine, though many other purine analogs are known and can be used as well. The agent that depletes intracellular ATP can be an adenylyl cyclase activator. Preferred agents include isoproterenol (isoprenaline) though other ATP depleting agents may be used.

In addition to isoprenaline that induces intracellular ATP depletion through activation of α2 adrenergic receptors transforming ATP to cAMP, antifolates which are a class of antimetabolite medications that antagonise the actions of folic acid, also induce intracellular ATP depletion through purine biosynthesis inhibition; such compounds include methotrexate, LY309887 and AG2034 and are incorporated by reference to hypertext transfer protocol secure:// www.ncbi.nlm.nih.gov/pubmed/29420256; and hypertext transfer protocol secure: //www.ncbi.nlm.nih.gov/pubmed/ 10656458 (last accessed Sep. 18, 2019).

In some embodiments, the purine analog comprises fludarabine which is administered in an amount ranging from 5, 10, 20, 30, 40 to 50 mg/m$^2$ and the agent that depletes intracellular ATP is isoproterenol which is administered in an amount ranging from 0.02, 0.03, 0.04, 0.05 to 0.06 mg.

In other embodiments of this method the purine analog comprises fludarabine and the agent that depletes intracellular ATP comprises LY309887, methotrexate or antifolate that functionally deplete intracellular ATP. In one embodiment the purine analog is fludarabine which is administered in an amount ranging from 5, 10, 20, 30, 40, to 50 mg/m$^2$ and the agent that depletes intracellular ATP is LY309887 which is administered in an amount ranging from 1, 2, 5, 10, 20, 30, 40 to 50 mg. These dosages may be administered as a bolus or over a period of time such as over a 15, 30, 45 or 60 minute period. They may be repeated as often as deemed necessary, for example, every 6, 12, 24, 35, or 48 hours for a period of 1, 2, 3, 4, 5, 6 or more weeks.

In some embodiments, the method involves administering other anticancer agents besides purine analogs and ATP depleting agents. These may include PDE inhibitors or other anticancer drugs. In other embodiments, the method consists or, or consists essentially of administering one or more purine analogs and one or more ATP depleting agents.

In some embodiments of this method the patient has a cancer whose ATP levels can be substantially depleted by the ATP depleting agent. Cancers include leukemia, lymphomas, such as chronic lymphocytic leukemia (CLL), chronic myeloid leukemia (CML), acute lymphocytic leukemia (ALL), acute myeloid leukemia (AML) or Hairy cell leukemia (HCL).

The cancer patient may be a child or adult such as a person that is at least 0, 1, 2, 3, 4, 5, 6, 7, 8, 9, 10, 20, 30, 40, 50, 60, 70, 80, 90 or >90 years of age. The patient may be male or female. The patient may have a primary or disseminated cancer which may be active or in remission. Some patients have developed a resistance to anticancer drugs such as purine analogs like fludarabine that decreases the efficacy of treatment with the agent.

Another embodiment of the invention is directed to a method for selecting a cancer patient for treatment with a purine analog comprising determining whether an agent that depletes intracellular ATP in normal cells depletes intracellular ATP in cancer cells from the patient, selecting a patient having cancer cells whose intracellular ATP is depleted by said agent, and treating the cancer patient with an agent that depletes intracellular ATP and with a purine analog. In some embodiments, a patient whose cancer cells undergo a depletion of intracellular ATP to 1, 2, 5, 10, 20, 30, 40, 50, 60, 70, 80, 90, 95 or <100% of a control level from untreated cancer cells or untreated normal tissue is selected. Preferably, intracellular ATP levels in the cancer cells are reduced to no more than 50% of control levels. Any ATP depleting agent may be employed by this method; preferably the ATP depleting agent is isoproterenol, LY309887 or methotrexate.

In some embodiments of this method the cancer is leukemia or lymphoma, such as CLL, CIVIL, ALL or AML or other types of cancer disclosed herein. This method may be used to select patients that have a type of cancer that is typically treated with a purine analog such as fludarabine, which is mainly used to treat chronic lymphocytic leukemia (CLL). It may also be used in trials for low grade non-Hodgkin lymphoma (NHL), hairy cell leukemia, acute myeloid leukemia and a type of lymphoma that affects the skin called mycosis fungoides.

Purine analogue-based chemotherapeutic drugs are used in the treatment of different cancers. Some representative drugs include the following.

Cladribine which is used for the treatment of active hairy cell leukemia, also used as an alternative agent for the treatment of chronic lymphocytic leukemia (CLL), low-grade non-Hodgkin's lymphoma, and cutaneous T-cell lymphoma. Tioguanine which is used for the treatment of acute non-lymphocytic leukemia. Clofarabine which is used for the treatment of pediatric patients 1 to 21 years old with relapsed or refractory acute lymphocytic leukemia (ALL). Mercaptopurine which is used for remission induction and maintenance therapy of acute lymphatic leukemia (ALL).

Nelarabine: Used for the treatment of pediatric and adult patients with acute T-cell lymphoblastic leukemia and T-cell lymphoblastic lymphoma whose disease has not responded to or has relapsed following treatment with at least two chemotherapy regimens. In some embodiments of the invention one or more of these purine analogs may be used in place of or may be used in conjunction with fludarabine.

Figure 7:
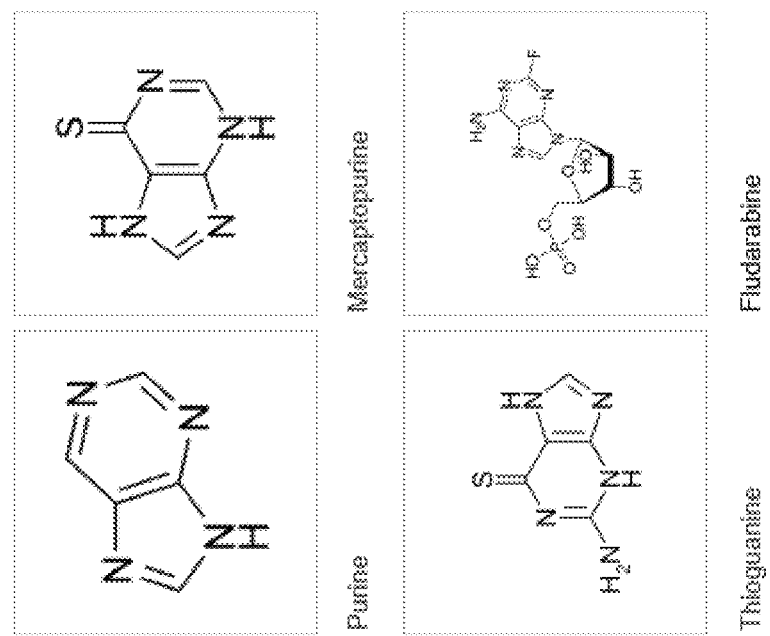
FIG. 7. Some purine and purine analog chemical structures.

Purine analogs include those described by and incorporated by reference to Parker, Chem Rev. 2009 July; 109(7): 2880-2893. doi: 10.1021/cr900028p. Purine analogs include thiopurines like thioguanine, azathioprine which is cleaved into 6-mercaptopurine, mercaptopurine, fludarabine, pentostatin and cladribine. Structures of purine and some representative purine analogs appear in FIG. 7.

Azathioprine is an immunosuppressive cytotoxic substance that is widely used after an organ or tissue transplantation to control rejection reactions. It is nonenzymatically cleaved to 6-mercaptopurine that acts as a purine analogue and an inhibitor of DNA synthesis. By preventing the clonal expansion of lymphocytes in the induction phase of the immune response, it affects both the cell and the humoral immunity. It also successfully suppresses autoimmunity. Mercaptopurine sold under the brand name Purinethol among others, is a medication used for cancer and autoimmune diseases. Specifically, it is used to treat acute lymphocytic leukemia (ALL), chronic myeloid leukemia (CML), Crohn's disease, and ulcerative colitis. Thiopurines such as thioguanine are used to treat acute leukemia and remissions in acute granulocytic leukemia. Fludarabine inhibits function of multiple DNA polymerases, DNA primase, and DNA ligase I, and is S phase-specific (since these enzymes are highly active during DNA replication). Pentostatin and cladribine are adenosine analogs that are used primarily to treat hairy cell leukemia. Other purine analogs that may be used in the invention include those described by hypertext transfer protocol://en.wikipedia.org/wiki/Purine_analogue—incorporated herein by reference.

Typically, a purine analog is a compound that is an antimetabiolite that mimics the structure of a metabolic purine. While bendamustine is not usually considered a purine analog, it does contain a purine-like benzimidazole ring, has some properties of a purine analog, and can be used in some embodiments of the invention in place of or in addition to a purine analog. Bendamustine, sold under the brand name Treanda among others is a chemotherapy medication used in the treatment of chronic lymphocytic leukemia, multiple myeloma, and non-Hodgkin's lymphoma. It is typically given by injection into a vein. It acts as an alkylating agent causing intra-strand and inter-strand cross-links between DNA bases.

Agents that deplete ATP include isoproterenol (isoprenaline), methotrexate, LY309887, NKH477 (colforsin dapropate hydrochloride), and other drugs that convert ATP into cAMP. Xu, et al., Cancer Res 2005; 65: (2). Jan. 15, 2005 (incorporated by reference) used inhibitors of glycolysis such as 3-BrPA (3-bromopyruvate) to block the major metabolic pathway by which the respiration-deficient cancer cells generate their ATP. 3-BrPA (3-bromopyruvate) is a pyruvate acid analog and an inhibitor of hexokinase II with a potent inhibitory effect on glycolysis. 3-BrPA and other inhibitors include phloretin, quercetin, STF31, WZB117, 3PO, 3-bromopyruvate, dichloroacetate, oxamic acid, and NHI-1. These inhibitors of glycolysis may be used in the invention, for example, in combination with fludarabine or another purine analog. Many of these agents convert ATP into cAMP which can exert a proapototic effect in some types of cancer cells.

$\beta_2$ (beta$_2$) adrenergic receptor agonists, also known as adrenergic $\ominus_2$ receptor agonists, are a class of drugs that act on the $\beta_2$ adrenergic receptor. Like other $\beta$ adrenergic agonists, they cause smooth muscle relaxation. $\beta_2$ adrenergic agonists' effects on smooth muscle cause dilation of bronchial passages, vasodilation in muscle and liver, relaxation of uterine muscle, and release of insulin. They are primarily used to treat asthma and other pulmonary disorders, such as COPD.

Indacaterol (INN) is an ultra-long-acting beta-adrenoceptor agonist. Such drugs are usually prescribed for moderate-to-severe persistent asthma patients or patients with chronic obstructive pulmonary disease (COPD).

Other ($3_2$ (beta$_2$) adrenergic receptor agonists which may be employed along with, or as substitutes for isoproterenol, include short-acting β2 agonists (SABAs) including bitolterol—Tornalate, fenoterol—Berotec, levosalbutamol (INN) or levalbuterol (USAN)—Xopenex, orciprenaline (INN) or metaproterenol (USAN)—Alupent, pirbuterol—Maxair, procaterol, ritodrine—Yutopar, salbutamol (INN) or albuterol (USAN)—Ventolin, terbutaline—Bricanyl; long-acting β2 agonists (LABAs) including arformoterol—Brovana, bambuterol—Bambec, Oxeol, clenbuterol—Dilaterol, Spiropent, formoterol—Foradil, Oxis, Perforomist, salmeterol—Serevent; Ultra-long-acting β2 agonists including abediterol, carmoterol, indacaterol—Arcapta Neohaler (U.S.), Onbrez Breezhaler (EU, RU), olodaterol—Striverdi Respimat, vilanterol with umeclidinium bromide—Anoro Ellipta, with fluticasone furoate—Breo Ellipta (U.S.), Relvar Ellipta (EU, RU); or those with an unknown duration of action including isoxsuprine, mabuterol, or zilpaterol—Zilmax.

Not all beta-adrenoceptor agonists induce intracellular ATP depletion and they can have different modes of action. Some agonists were tested that had no effect on intracellular ATP level and others had very limited effect. Indacaterol (INDA) induced a moderate ATP depletion by comparison to isoproterenol.

The term "treat" and corresponding terms such as "treatment" and "treating" include therapeutic treatment as well as palliative, restorative, and preventative treatment of a subject. The term "therapeutic treatment" refers to treatment that halts the progression of, reduces the pathologic manifestations of, reduces the severity of, or entirely eliminates a condition in a subject. The term "palliative treatment"

refers to treatment that eases or reduces the effect or intensity of a condition in a subject without curing the condition.

The term "preventative treatment" (and the corresponding term "prophylactic treatment") refers to treatment that prevents the occurrence of a condition in a subject. The compositions as disclosed herein may be used for either therapeutic, palliative treatment, or preventative treatment of cancers including leukemia or lymphoma.

A "chemotherapeutic agent" refers to individual agents, such as fluadrabine or isoproterenol, as well as combinations of such agents such as an agent that comprises both fludarabine and isoproterenol. This term encompasses the use of other anticancer drugs or combinations of anticancer drugs, such as a regimen that involves an agent that comprises two, three, four or more drugs or individual agents. This term encompasses agents that effect therapeutic or preventative treatments as described herein.

An "effective amount" of a compound with respect to the subject method of treatment refers to an amount of the compound(s) in a preparation which, when administered as part of a desired dosage regimen, for example, to a mammal, such as a human, alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment. In an embodiment, an effective amount of a purine analog is an amount the inhibits growth, nucleic acid replication, or protein expression of a cell and a therapeutically effective amount of a drug that depletes ATP is one that significantly lowers ATP level inside of a cell or which increases the efficacy (e.g, cytotoxicity) of a purine analog that is administered with it. An effective amount may be sufficient to exert a therapeutic treatment or preventative treatment as described herein.

In some embodiments, fludarabine is administered intravenously in a dosage range for 1, 2, 5, 10, 20, 30, 40, 50, 60, 70, 80, 90 to 100 mg/m$^2$, preferably, from 5 to 50 mg/m$^2$, and more preferably at about 25 mg/m$^2$ for an adult patient. This dosage may be administered over a period of about 15 to 60 minutes each day over a period of 1, 2, 3, 4, 5, 6, 7, 8, 9 or 10 days, preferably over a period of about 5 days. This regimen may be repeated every 2, 3, 4, 5, or 6 weeks. Fludarabine dosage may be decreased or delayed based on evidence of hematologic or nonhematologic toxicity and can be discontinued if neurotoxicity develops. Preferably, these dosages of fludarabine are administered with a dosage of an ATP-depleting drug such as isoproterenol sufficient to reduce intracellular ATP levels to 10, 20, 30, 40, 50, 60, 70, 80, or 90% of control (untreated) levels or a dosage of isoproterenol ranging from about 0.02 to 0.06 mg. In some embodiments a daily dosage of the purine analog, such as fludarabine, can range from about 0.025, 0.05, 0.1, 0.25, 0.5, 1.0 to 2.5 preferably about 0.25 mg/m$^2$. In some preferred embodiments this dosage may be continued daily for 1, 2, 3, 4, 5, 6, 7, 8, 9, 10 or more days, preferably for about 5 days as an i.v. infusion.

The inventors have found that primary CLL cells treated with isoprenaline at a concentration of 30 µM for 12 hours were depleted for more than 80% of their intracellular ATP, In vivo a medical practitioner would select a dosage no more than a maximum tolerated dose which avoids detrimental side-effects on the heart, for example, a dosage of about 0.25, 0.5, 0.75, 1.0, 1.5 or 2.0 depending on the size and condition of the patient. Higher dosages than those used in vivo may be used for ex vivo treatment of cells such as stem cells, hematopoietic cells or other cells that may be treated ex vivo and then reinfused or replaced into the patient.

In some embodiments, other drugs may be used to deplete ATP. For example, LY309887 and methotrexate may be used to deplete ATP. Moreover, these two drugs are often tolerated more and less toxic than isoproterenol, Thus, for example, a combination of methotrexate and tiudarabine or LY309887 and fludarabine may be used according to the invention. The concentrations of these drugs would also be used in vivo at or below their maximum tolerated dosages or at higher concentrations for ex vivo procedures.

A dosage of isoproterenol sufficient to deplete intracellular ATP in target cancer cells to less than or equal to 1, 2, 5, 10, 20, 30, 40, 50, 60, 70, 80, 90 or <100% of a control level such as the level in untreated cancer cells or in normal cells, may be selected by those of skill in the art, for example, using the methods exemplified herein. In some embodiments, isoproterenol dosage may range from 0.01, 0.02, 0.03, 0.04, 0.05, 0.06, 0.07, 0.08, 0.09, to 0.1 mg, preferably from 0.02 to 0.06 mg. Dosage may be administered i.v. in a pharmaceutically acceptable excipient such as saline or dextrose solution.

A phosphodiesterase inhibitor is a drug that blocks one or more of the five subtypes of the enzyme phosphodiesterase (PDE), thereby preventing the inactivation of the intracellular second messengers cyclic adenosine monophosphate (cAMP) and cyclic guanosine monophosphate (cGMP) by the respective PDE subtype(s). In some embodiments a PDE inhibitor or other cancer drug may be coadministered with the agent that depletes ATP and the purine analog. In other embodiments, a PDE inhibitor or other anticancer drug is not coadministered to a cancer patient.

The terms "prevent", "prevention", or "preventing" refer to either preventing the onset of preclinically evident condition altogether or preventing the onset of a preclinical evident stage of a condition in a subject. Prevention includes, but is not limited to, prophylactic treatment of a subject at risk of developing a condition. This term may also refer to prevention of progression or exacerbation of a disease, disorder or condition or prevention of a symptom of a disease, disorder or condition. The compositions as disclosed herein may be used to prevent development of, or relapse of, cancers including leukemia or lymphoma.

A composition as disclosed herein may include one or both active ingredients, for example, an i.v. solution containing both isoproterenol and fludarabine will contain both active ingredients, while individual solutions of isoproterenol and fludarabine may be prepared and administered simultaneously or one before the other. Preferably, for treatment of leukemia and lymphoma and other non-solid cancers, the composition will be in a form suitable for parenteral administration, for example, in a form that can be administered i.v., However, pharmaceutical formulations of the present invention include those suitable for oral, rectal, nasal, topical (including buccal and sublingual), subcutaneous, vaginal or parenteral (including intramuscular, subcutaneous and intravenous) administration or a form suitable for administration by inhalation or insufflation. Examples of oral formulations comprising the composition of the present invention as an active ingredient include tablets, troches, lozenges, aqueous or emulsified suspensions, powders, granules, emulsions, hard or soft capsules, syrups, or elixirs. Formulations such as tablets or capsules may include a binder such as lactose, saccharose, sorbitol, mannitol, starch, amylopectin, cellulose or gelatin, an expedient such as dicalcium phosphate, a disintegrant such as corn starch or sweet potato starch, and a lubricant such as magnesium stearate, calcium stearate, sodium stearyl fumarate or polyethylene glycol wax. Capsule formulations may comprise, in addition to the above-mentioned substances, a liquid carrier such as fatty oil.

Parenteral formulations comprising the composition of the present invention as an active ingredient include injectable forms for subcutaneous, intravenous or intramuscular injection, suppositories, or sprays inhalable via the respiratory organ, such as aerosols. Injectable formulations may be prepared by mixing the composition of the present invention with a stabilizer or a buffer in water to prepare a solution or a suspension, and loading the solution or suspension into ampules or vials to prepare unit dosage forms. Suppository formulations include suppositories or retention enemas, e.g. containing conventional suppository bases such as cocoa buffer or other glycerides. For spray formulations, such as aerosols, a propellant for spraying a water-dispersed concentrate or wet powder may be used in combination with an additive.

"Synergy" or "synergism" refers to an interaction between two or more drugs that causes the total effect of the drugs to be greater than the sum of the individual effects of each drug. In some embodiments a synergistic effect may exceed the total effect of both drugs on one or more symptoms or, mechanisms or other characteristics of a disease, disorder, or condition by 5, 10, 20, 30, 40, 50, 60, 70, 80, 90, 100 or >100%. For example, depletion of intracellular ATP in a cancer cell by a drug can increase the affinity of a purine analog to the cancer cell and enhance its anticancer activity. Thus, the combination of an ATP depleting drug and a purine analog like fludarabine can exhibit an anticancer effect that exceeds the anticancer of each drug in combination as shown by FIG. 2 (compare last two bars).

The terms "inhibit", "inhibiting", and "inhibition" refer to the slowing, halting, or reversing the growth or progression of a disease, infection, condition, or group of cells. The inhibition can be greater than about 5, 10, 20%, 40%, 60%, 80%, 90%, 95%, or 99%, for example, compared to the growth or progression that occurs in the absence of the treatment or contacting. The compositions as disclosed herein may be to inhibit the development, progression, or dissemination of cancers including leukemia or lymphoma.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo. Contacting includes bringing the compositions disclosed herein, such as a combination of fludarabine and isoproterenol, with cancer cells, for example, by i. v. infusion or bolus administration. Other modes of administration may also be used to contact cancer cells with a composition as disclosed herein including, where appropriate, in situ administration into a compartment containing cancer cells or into a cancer cell mass for solid cancers. Other routes of administration include oral and parenteral, such as by injection, inhalation, or by a transdermal, intravenous, intranasal, intracranial, and/or intrathecal route.

Contacting may also occur ex vivo, for example, when the hematopoietic cells or other cells are removed from a patient treated as disclosed herein with an agent that depletes ATP and with a purine analog such as fludarabine, and then reinfused or replaced into the patient. One advantage of an ex vivo procedure is that cells may be subjected to higher doses of drugs such as fludarabine and isoproterenol that would not be tolerated or that could be toxic to other bodily tissues if administered in vivo.

The term "exposing" is intended to encompass definitions as broadly understood in the art. In an embodiment, the term means to subject or allow to be subjected to an action, influence, or condition. For example and by way of example only, a cell can be subjected to the action, influence, or condition of a therapeutically effective amount of a pharmaceutically acceptable form of a chemotherapeutic agent.

The term "cancer cell" is intended to encompass definitions as broadly understood in the art. In an embodiment, the term refers to an abnormally regulated cell that can contribute to a clinical condition of cancer in a human or animal. In an embodiment, the term can refer to a cultured cell line or a cell within or derived from a human or animal body. A cancer cell can be of a wide variety of differentiated cell, tissue, or organ types as is understood in the art. The term "tumor" refers to a neoplasm, typically a mass that includes a plurality of aggregated malignant cells.

Leukemia includes the following types of leukemia which may be treated by a composition as disclosed herein.

Acute lymphocytic leukemia (ALL) progresses rapidly, replacing healthy cells that produce functional lymphocytes with leukemia cells that can't mature properly. The leukemia cells are carried in the bloodstream to other organs and tissues, including the brain, liver, lymph nodes and testes, where they continue to grow and divide. The growing, dividing and spreading of these leukemia cells may result in a number of possible symptoms.

Acute myeloid leukemia (AML), also known as acute myelogenous leukemia, acute myeloblastic leukemia, acute granulocytic leukemia or acute nonlymphocytic leukemia, is a fast-growing form of cancer of the blood and bone marrow.

Chronic lymphocytic leukemia (CLL) is a typically slow-growing cancer that begins in lymphocytes in the bone marrow and extends into the blood. It may also spread to lymph nodes and organs such as the liver and spleen. CLL develops when too many abnormal lymphocytes grow, crowding out normal blood cells and making it difficult for the body to fight infection.

Chronic myeloid leukemia (CML), also known as chronic myelogenous leukemia, begins in the blood-forming cells of the bone marrow and then, over time, spreads to the blood. Eventually, the disease spreads to other areas of the body.

Hairy cell leukemia (HCL) is a rare subtype of chronic lymphocytic leukemia (CLL) that progresses slowly. HCL is caused when bone marrow makes too many B cells (lymphocytes), a type of white blood cell that fights infection. As the number of leukemia cells increases, fewer healthy white blood cells, red blood cells and platelets are produced.

Myelodysplastic syndromes (MDS) are a group of closely related diseases in which the bone marrow produces too few functioning red blood cells (which carry oxygen), white blood cells (which fight infection), or platelets (which prevent or stop bleeding), or any combination of the three. The different types of myelodysplastic syndromes are diagnosed based on certain changes in the blood cells and bone marrow. The cells in the blood and bone marrow (also called myelo) usually look abnormal (or dysplastic), hence the name myelodysplastic syndromes.

The compositions disclosed herein may be used to treat leukemia, lymphomas and other cancers alone or in combination with other methods or agents, such as other chemotherapeutic agents, biological agents that help the immune system recognize and attack leukemia cells, targeted therapy that uses drugs that attack specific vulnerabilities within one's cancer cells, such as the drug imatinib (Gleevec)

which stops the action of a protein within the leukemia cells of people with chronic myelogenous leukemia, with radiation therapy, or prior to stem cell transplant. Drugs used to treat leukemia include those described below:

Acute Lymphoblastic Leukemia (ALL): Arranon (Nelarabine), Asparaginase Erwinia chrysanthemi, Asparlas (Calaspargase Pegol-mknl), Besponsa (Inotuzumab Ozogamicin), Blinatumomab, Blincyto (Blinatumomab), Calaspargase Pegol-mknl, Cerubidine (Daunorubicin Hydrochloride), Clofarabine, Clolar (Clofarabine), Cyclophosphamide, Cytarabine, Dasatinib, Daunorubicin Hydrochloride, Dexamethasone, Doxorubicin Hydrochloride, Erwinaze (Asparaginase Erwinia Chrysanthemi), Gleevec (Imatinib Mesylate), Iclusig (Ponatinib Hydrochloride), Inotuzumab Ozogamicin, Imatinib Mesylate, Kymriah (Tisagenlecleucel), Marqibo (Vincristine Sulfate Liposome), Mercaptopurine, Methotrexate, Nelarabine, Oncaspar (Pegaspargase), Pegaspargase, Ponatinib Hydrochloride, Prednisone, Purinethol (Mercaptopurine), Purixan (Mercaptopurine), Rubidomycin (Daunorubicin Hydrochloride), Sprycel (Dasatinib), Tisagenlecleucel, Trexall (Methotrexate), Vincristine Sulfate, Vincristine Sulfate Liposome.

Acute Myeloid Leukemia (AML): Arsenic Trioxide, Cerubidine (Daunorubicin Hydrochloride), Cyclophosphamide, Cytarabine, Daunorubicin Hydrochloride, Daunorubicin Hydrochloride and Cytarabine Liposome, Daurismo (Glasdegib Maleate), Dexamethasone, Doxorubicin Hydrochloride, Enasidenib Mesylate, Gemtuzumab Ozogamicin, Gilteritinib Fumarate, Glasdegib Maleate, Idamycin PFS (Idarubicin Hydrochloride), Idarubicin Hydrochloride, Idhifa (Enasidenib Mesylate), Ivosidenib, Midostaurin, Mitoxantrone Hydrochloride, Mylotarg (Gemtuzumab Ozogamicin), Rubidomycin (Daunorubicin Hydrochloride), Rydapt (Midostaurin), Tabloid (Thioguanine), Thioguanine, Tibsovo (Ivosidenib), Trisenox (Arsenic Trioxide), Venclexta (Venetoclax), Venetoclax, Vincristine Sulfate, Vyxeos (Daunorubicin Hydrochloride and Cytarabine Liposome), Xospata (Gilteritinib Fumarate).

Chronic Lymphocytic Leukemia (CLL): Alemtuzumab, Arzerra (Ofatumumab), Bendamustine Hydrochloride, Bendeka (Bendamustine Hydrochloride), Campath (Alemtuzumab), Chlorambucil, Copiktra (Duvelisib), Cyclophosphamide, Dexamethasone, Duvelisib, Fludarabine Phosphate, Gazyva (Obinutuzumab), Ibrutinib, Idelalisib, Imbruvica (Ibrutinib), Leukeran (Chlorambucil), Mechlorethamine Hydrochloride, Mustargen (Mechlorethamine Hydrochloride), Obinutuzumab, Ofatumumab, Prednisone, Rituxan (Rituximab), Rituxan Hycela (Rituximab and Hyaluronidase Human), Rituximab, Rituximab and Hyaluronidase Human, Treanda (Bendamustine Hydrochloride), Venclexta (Venetoclax), Venetoclax, and Zydelig (Idelalisib).

Chronic Myelogenous Leukemia (CIVIL): Bosulif (Bosutinib), Bosutinib, Busulfan, Busulfex (Busulfan), Cyclophosphamide, Cytarabine, Dasatinib, Dexamethasone, Gleevec (Imatinib Mesylate), Hydrea (Hydroxyurea), Hydroxyurea, Iclusig (Ponatinib Hydrochloride), Imatinib Mesylate, Mechlorethamine Hydrochloride, Mustargen (Mechlorethamine Hydrochloride), Myleran (Busulfan), Nilotinib, Omacetaxine Mepesuccinate, Ponatinib Hydrochloride, Sprycel (Dasatinib), Synribo (Omacetaxine Mepesuccinate), and Tasigna (Nilotinib).

One or more of the above anti-cancer agents may be used in addition to a composition according to the invention, such as a composition containing both isoproterenol and fludarabine or their equivalents.

Example 1

Isoproterenol does not Induce Cell Death in Primary CLL Cells but it Induces a Long-Lasting Dose-Dependent Intracellular ATP Depletion and Intracellular cAMP Accumulation Primary CLL cells were treated with 3 uM isoproterenol ($IC_{50}$ determined with Cell-titer Glo® assay) for 24 hr. Cell death markers for apoptosis (cleaved PARP, cleaved caspase 3 and caspase 9) and autophagy (accumulation of LC3 II) were assessed by western blotting. The non-competitive selective phosphodiesterase inhibitor, IBMX, was used as a positive control because it induces apoptosis in CLL B cells. Results are shown in FIG. 1A. NT (not treated) and Iso (treated with isoproterenol) show similar patterns with no cleaved PARP, while the positive apoptosis control (IBMX) shows the presence of cleaved PARP.

Figure 1B:
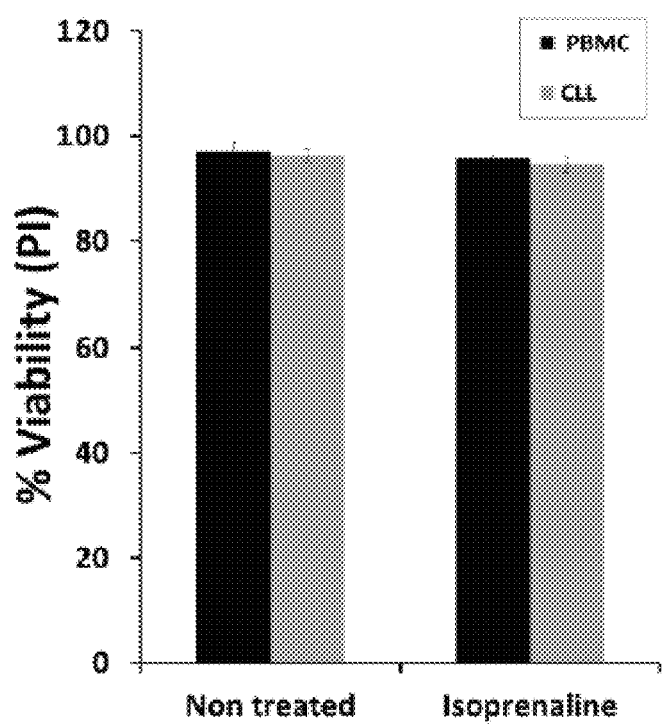
FIG. 1B. Comparison of isoproterenol-induced cell death in normal PBMC (black blocks) and in primary CLL cells (gray Blocks) by propidium iodide staining and flow cytometry analysis.

To assess viability of the treated cells, cells were stained by propidium iodide and analyzed by flow cytometry. FIG. 1B shows similar viability for normal PBMCs (black bars) and CLL cells (gray bars) after isoproterenol treatment. These results confirm that isoproterenol treatment (3 uM) did not induce any significant cell death in normal PBMCs or in CLL primary cells.

The cytotoxic effects of contacting cells with a gradient of isoproterenol concentrations were assessed to provide dose-response data. Data were obtained using both an ATP-dependent cell-titer Glo® assay (dashed line in FIG. 1C) and with an ATP-independent PI/flow cytometry assay (solid line in FIG. 1C).

FIG. 1C shows the effect of Iso on cell viability using two different assays: MTT (ATP independent assay) and cell-titer Glo® (ATP-based assay). The two assays gave completely different dose-response curves. Higher concentrations of Iso lowered the luminescence indicating that the concentration of intracellular ATP was reduced. Intracellular ATP quantity is proportional to cell number and a decrease of intracellular ATP is usually due to cell death, but in this case cell number did not change that much as it is indicated by the MTT assay. All of these data taken together indicate that Iso doesn't induce cell death in CLL primary cells but induces intracellular ATP depletion.

CellTiter-Glo® Luminescent Cell Viability Assay is a homogeneous method for determining the number of viable cells in culture based on quantitation of the ATP present, an indicator of metabolically active cells.

The PI/flow cytometry assay assesses cell viability using propidium iodide (PI) which is a membrane impermanent dye that is generally excluded from viable cells. It binds to double stranded DNA by intercalating between base pairs.

As shown by the solid line in FIG. 1C, exposure of cells to 1 to 20 µM concentrations of isoproterenol (isoprenaline) did not induce cell death. However, these concentrations induced a dose-dependent decrease in luminescence in the cell-titer Glo® Assay® (dashed line) showing that isoproterenol (isoprenaline) induced intracellular ATP depletion.

Samples of primary ALL, AML, CLL and CIVIL leukemia cells were obtained and assayed for their expression of adrenergic receptors. Samples of normal PBMCs ("CTL") and the CLL cell line WA-C3CD5+ were also evaluated. Readings from all samples were obtained by quantitative real-time PCT or qPCR. The control cells described by FIG. 1D were normal PBMCs from a healthy donor.

As shown by FIG. 1D, all cells expressed β2AR (beta-2 adrenergic receptor or $β_2$ adrenoreceptor) with CLL cell line WA-C3CD5+ expressing the least.

With the exception of the AML sample, β1AR (beta-1 adrenergic receptor or $\beta_1$ adrenoceptor), was expressed at very low levels.

β3AR (beta-3 adrenergic receptor, $\beta_3$ adrenoreceptor, not shown) was undetected in all samples.

These results show the presence of intracellular receptors that can interact with isoproterenol.

Figure 1E:
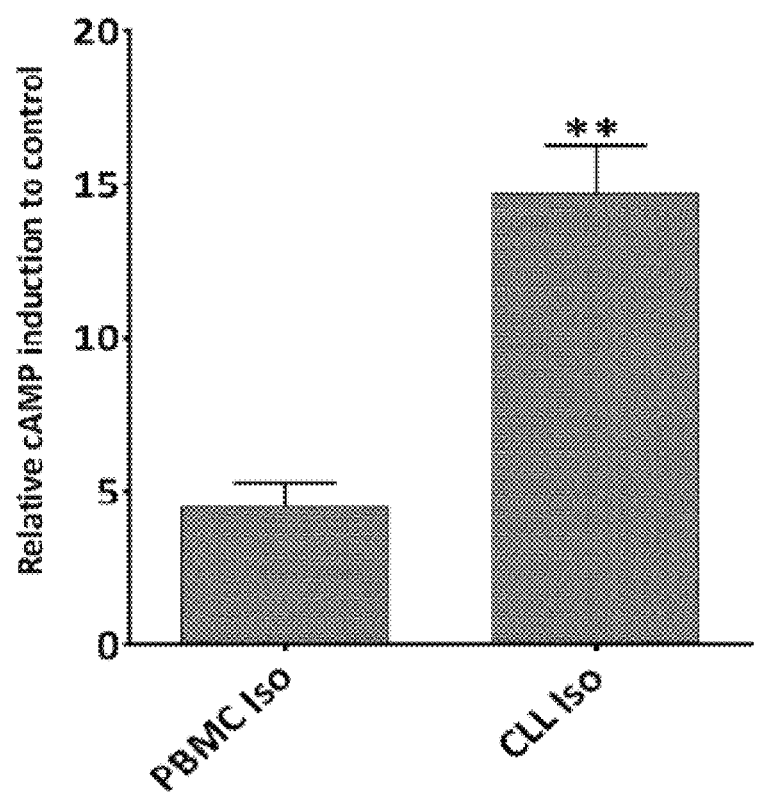
FIG. 1E. Isoproterenol-induced intracellular cAMP accumulation in normal PBMCs and primary CLL cells pre-treated for one hour with phosphodiesterase inhibitor (IBMX) and then with 10 uM Iso for 6 h.

Isoproterenol-induced intracellular cAMP accumulation in normal PBMCs and primary CLL cells was assessed. Cell samples were pre-treated for one hour with phosphodiesterase inhibitor (IBMX) and then with 10 uM isoproterenol for 24 hr. As shown in FIG. 1E, significantly higher accumulation of cAMP was observed in CLL cells treated with isoproterenol compared to normal cells. These results show a disproportionate ATP depleting effect of isoproterenol on CLL compared to normal cells.

Samples of primary CLL cells were treated in vitro with 20 μM isoproterenol for 24 hours in a human phosphokinase array. In the array each kinase was spotted in duplicate with hybridization signals at the corners serving as controls. Relative levels of protein phosphorylation (normalized intensity for each antibody) were calculated for each untreated and treated sample.

Figure 1F:
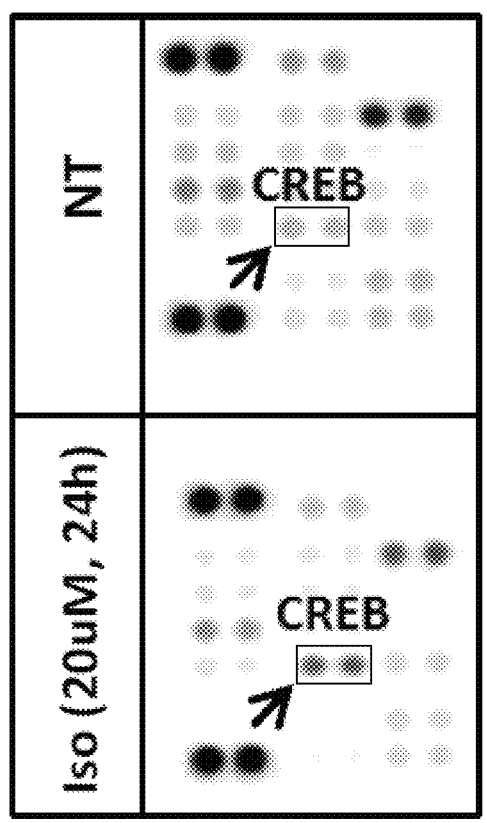
FIG. 1F. Human phosphokinase array reveals alteration in phosphorylation of kinases upon in vitro treatment of primary CLL cells with 10 uM Iso for 24 h. In the array each kinase is spotted in duplicate. Hybridization signals at the corners serve as control.

Results revealed an alteration in phosphorylation of kinases upon in vitro treatment with the isoproterenol compared to untreated ("NT") cells as shown by FIG. 1F. p-CREB (indicated by black arrow in FIG. 1F) was the only significantly up-regulated kinase upon isoproterenol treatment.

FIG. 1G shows level of p-CREB up-regulation based on relative mean pixel density.

Example 2

Figure 2A:
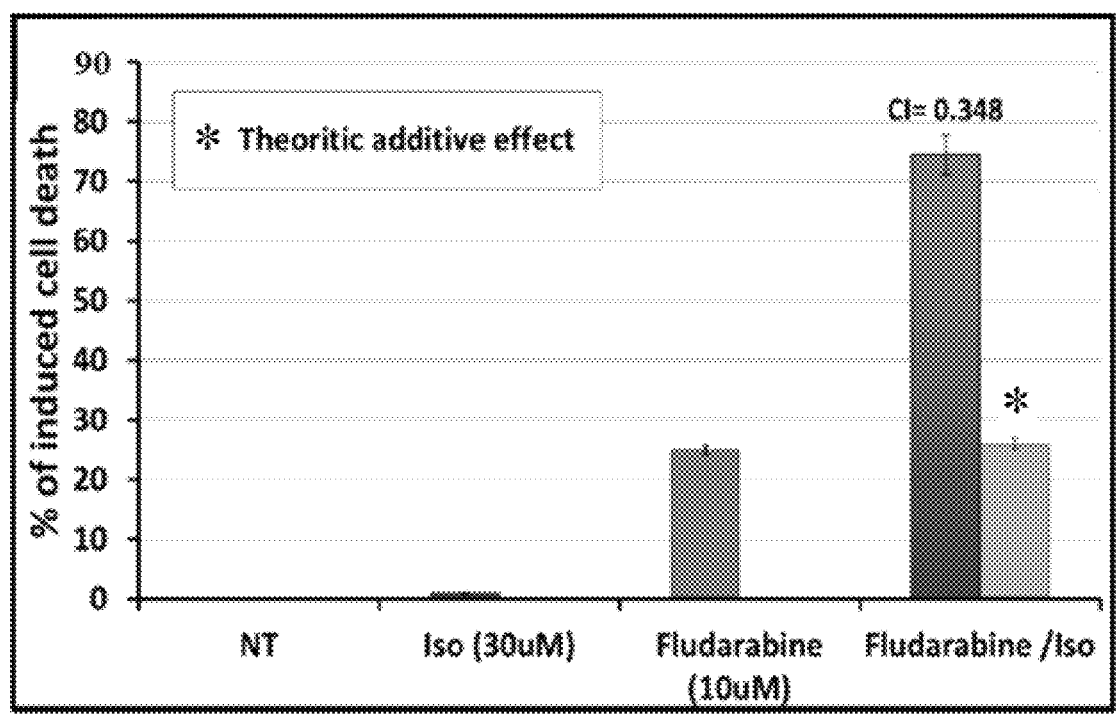
FIG. 2A. Cytotoxicity/cell growth inhibition of primary CLL cells, isolated from three CLL patients, by the purine analogue fludarabine (10 uM) alone or in combination with Isoproterenol (30 uM). Induced cell death was assessed by PI staining and flow cytometry analysis.
Figure 2W:
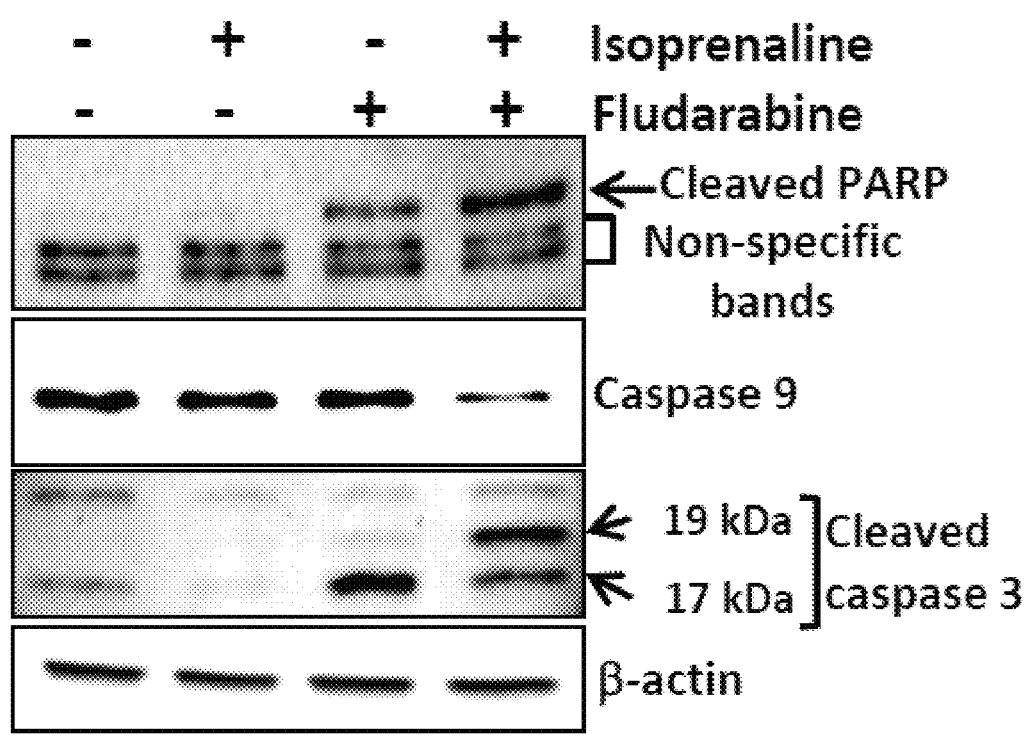
FIG. 2W. Control primary CLL cells and primary CLL cells pre-treated with isoproterenol (30 uM) for 12 h were incubated with 10 uM fludarabine for 48 h, cells were than harvested and examined by immunoblotting with the indicated apoptotic markers.

Isoproterenol Potentiates Effects of Fludarabine and Synergistically Induces Apoptotic Cell Death in Primary CLL Cells Primary CLL cells were isolated from three CLL patients and were exposed 10 uM fludarabine (a purine analog) alone or in combination with 30 uM isoproterenol to assess the effects of the drug(s) on cytotoxicity and growth. Induced cell death was assessed by PI staining and flow cytometry. As shown by FIG. 2A, addition of isoproterenol to fludarabine synergistically increased cytotoxicity compared to each drug alone or compared to the theoretical additive effects of each drug.

ATP depletion in CLL cells was measured by the ATP-based luminescent assay CellTiter-Glo®. A shown by FIG. 2B, increasing the concentration of isoproterenol increased intracellular ATP depletion of CLL cells.

Not treated (NT), isoproterenol-treated (Iso), fludarabine-treated (Flud), and cells treated with both drugs (Iso/flud) CLL cells were subjected to annexin V/PI staining. Staining with annexin V and propidium iodide (PI) identifies different types of cell death—either necrosis or apoptosis. This technique relies on two components. During apoptosis, phosphatidylserine (PS) is translocated from the cytoplasmic face of the plasma membrane to the cell surface. Annexin V has a strong, $Ca^{2+}$-dependent affinity for PS and therefore can be used as a probe for detecting apoptosis. PI is a membrane impermanent dye that is generally excluded from viable cells. As apparent from FIGS. 2C-2V, the treatment of the CLL cells with the combination of both fludarabine and isoproterenol significantly increased the numbers of cells taking up PI and staining with annexin indicating that this combination exerted superior cytotoxic and apoptotic effects.

Control primary CLL cells and primary CLL cells were pre-treated with 30 uM isoproterenol for 12 hrs and incubated with 10 uM fludarabine for 48 hr. Cells were then harvested and examined by immunoblotting with apoptotic markers Cleaved PARP and caspace 9. Apoptosis was not observed in control sample ($1^{st}$ lane) or in sample treated with isoproterenol alone. Apoptosis was observed in samples treated with fludarabine and with the combination of fludarabine and isoproterenol as described in FIG. 2W. Significantly more cleavage of caspace 3 was observed in the sample treated with both drugs.

Cleaved caspase 3 is a marker of apoptosis. As shown by the western blot banding patterns and intensity, a higher level of caspace 3 cleavage occurred in cells treated with the combination of isoproterenol and fludarabine compared to the amount of cleavage in cells treated with fludarabine alone. This shows that the combination of isoproterenol and fludarabine induced more cell death than fludarabine alone.

Example 3

Figure 3D:
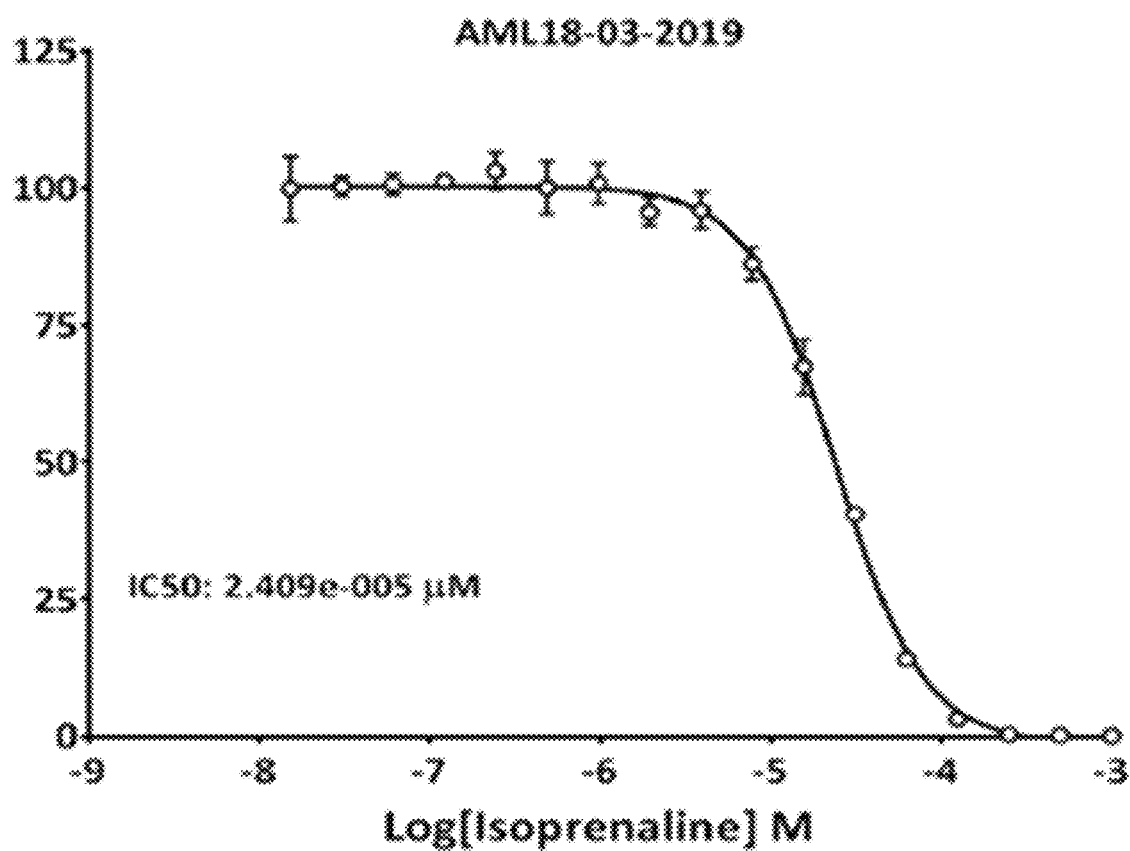

Sensitivity of Cells to Isoproterenol is Proportionate to Synergistic Effect Between Fludarabine and Isoproterenol Cells from CLL, AML, and from normal donors were treated with 30 μM isoproterenol, 10 μM fludarabine, or a mixture of both drugs at these concentrations as shown by FIGS. 3A, 3C and 3E respectively.

Isoproterenol-induced intercellular ATP depletion was determined by the ATP-based luminescent assay CellTiter-Glo®. The efficiency of isoproterenol in depleting intracellular ATP is represented by the dose response curves shown by FIGS. 3B, 3D and 3F respectively.

The indicated IC50 values were inversely proportional to the efficiency of intracellular ATP depletion and cell sensitivity to isoproterenol. As shown by FIG. 3A, primary CLL cells isolated from a CLL patient at early stage showed lesser sensitivity to isoproterenol and combinatorial treatment of these cells showed a relatively low synergistic effect. Similar phenomenon were observed in primary cells isolated from an AML patient and a normal donor as shown in FIGS. 3C and 3E, respectively. These results show that synergism between fludarabine and isoproterenol may be predicted from sensitivity of the cells to depletion of intracellular ATP by isoproterenol.

Example 4

Figure 5A:
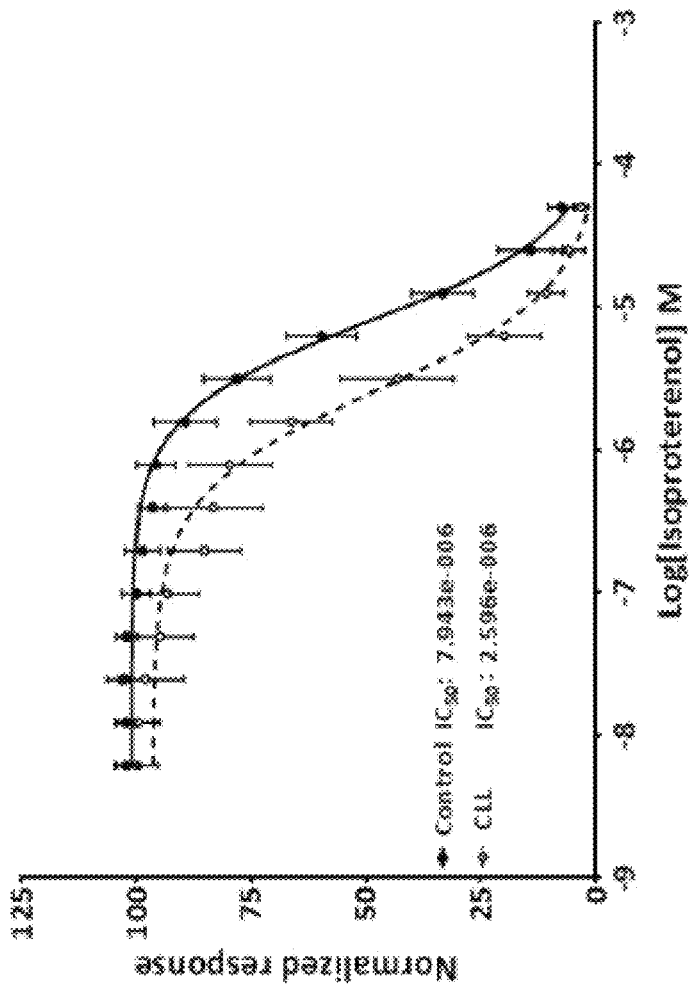
FIGS. 5A-5D. Dose response graphs of normalized ATP depletion responses to various concentrations of isoproterenol. Responses of CLL (FIG. 5A), CIVIL (FIG. 5B), AML (FIG. 5C) and ALL (FIG. 5D) cells were compared to those in normal PBMCs.
Figure 5B:
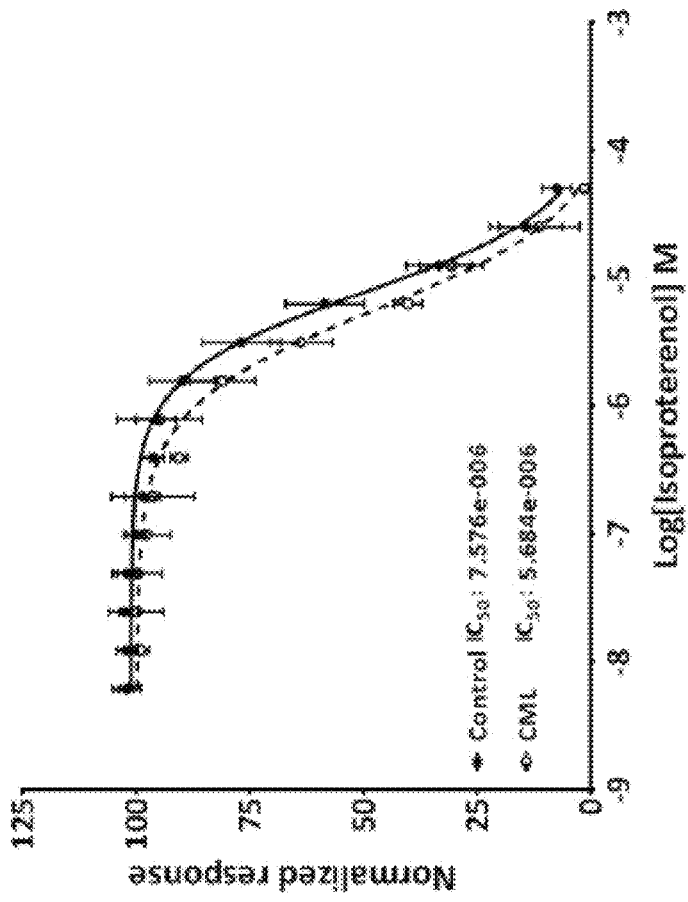
Figure 5C:
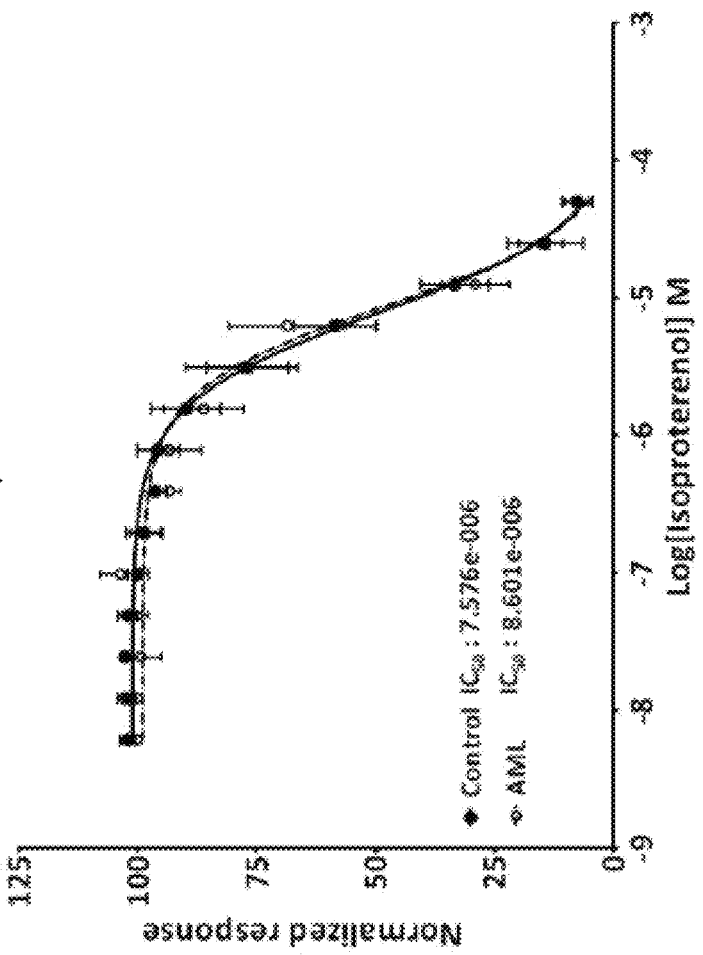
Figure 5D:
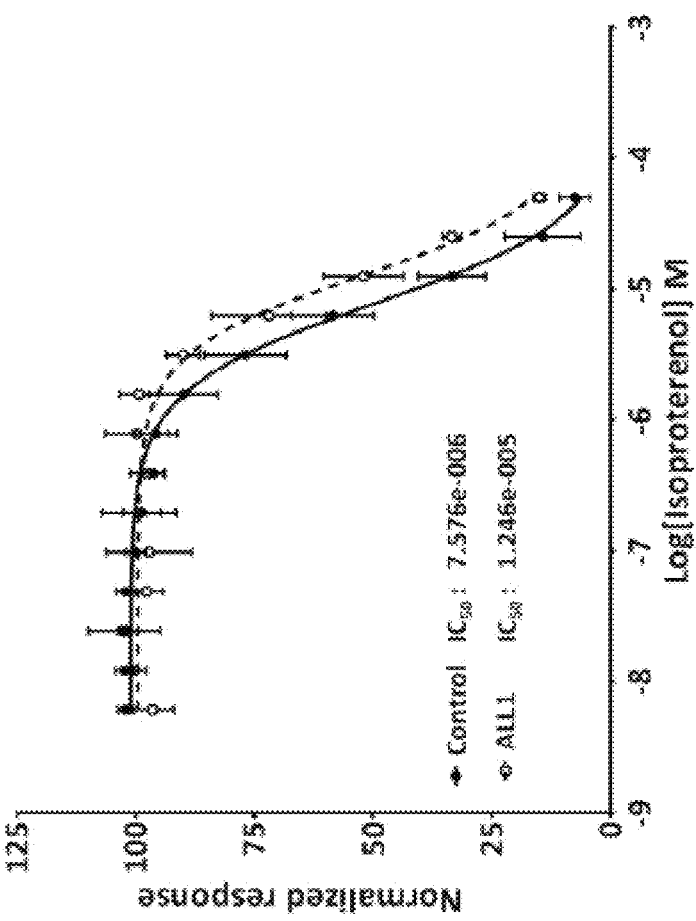

Isoproterenol (Isoprenaline) Induces Intracellular ATP Depletion in PBMC Isolated from all Leukemia Subtypes and from Normal Donors Isoproterenol-induced ATP depletion in chronic lymphocytic leukemia (CLL; FIG. 5A), chronic myeloid leukemia (CIVIL; FIG. 5B), AML; FIG. 5C) and acute lymphoblastic leukemia (ALL; FIG. 5D) was compared to the same effect in normal PBMCs.

Figure 5E:
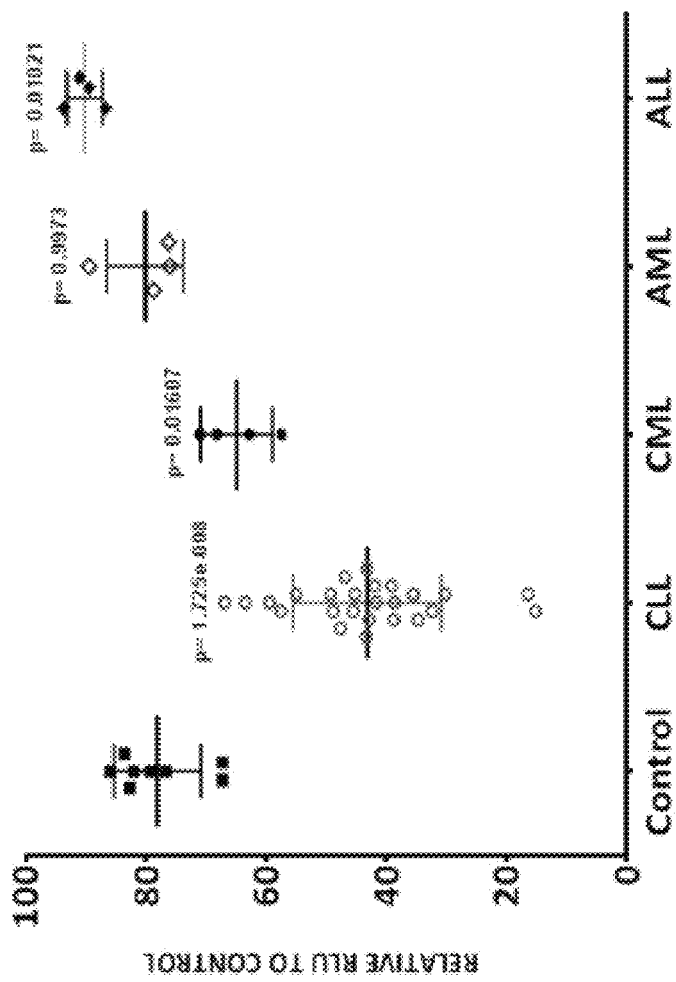
FIG. 5E. Relative ATP depletion by isoproterenol in normal, CLL, CML, AML and ALL cells.

CLL primary cells showed the highest sensitivity to isoproterenol induced intracellular ATP depletion (FIG. 5E) followed by CLL, ALL and AML cells respectively.

Example 5

Synergistic Effects of Other Compounds Inducing ATP Depletion

The effects of a beta adrenergic receptor agonist, indacaterol, to activate adenylyl cyclase and subsequently deplete ATP by converting it to cAMP were assessed. This agonist was used in combination with two purine analogues fludarabine and bendamustine to treat primary CLL cells.

After 24 hours treatment, the treated cells were stained with the cell-death marker, propidium iodide and analyzed with flow-cytometry to determine % induced cell death.

Results in FIG. 4 show that indacaterol, similarly to isoproterenol, produces a synergistic effect in combination with either of the two purine analogues fludarabine and bendamustine and that this cytotoxic effect of combinations is significantly higher than the sum of the two separate cytotoxic effects (theoretic additive effect).

Example 6

Isoproterenol Synergizes Specifically with the Purine Analogue Fludarabine in Dose-Dependent Manner The cytotoxic effect of isoproterenol/fludarabine combination on CLL primary cells was evaluated by the luminescent-based assay Cell-Titer Glo®. As shown by FIG. 6A, higher 10 µM concentrations of isoproterenol produced superior cytotoxic effects in combination with fludarabine or doxorubicin. As shown by FIG. 6A, when different concentrations of isoproterenol (1 µM and 10 µM) were combined with increasing doses of fludarabine, a synergistic effect was observed when the isoproterenol concentration was higher than 1 µM. A concentration of 1 µM produced a weak intracellular ATP depletion. When a 10 µM concentration of isoproterenol was combined with fludarabine a highly synergistic effect was observed in concentrations ranging from 0.1 µM to 50 µM (see FIG. 6A).

Figure 6B:
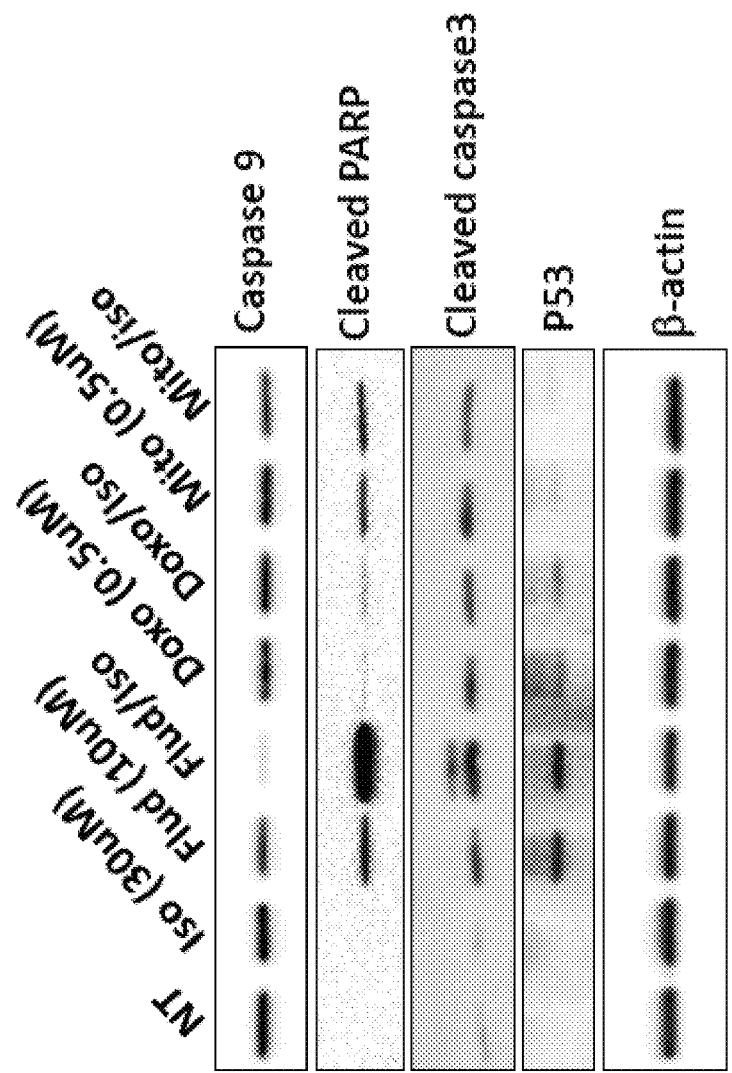
Figure 6C:
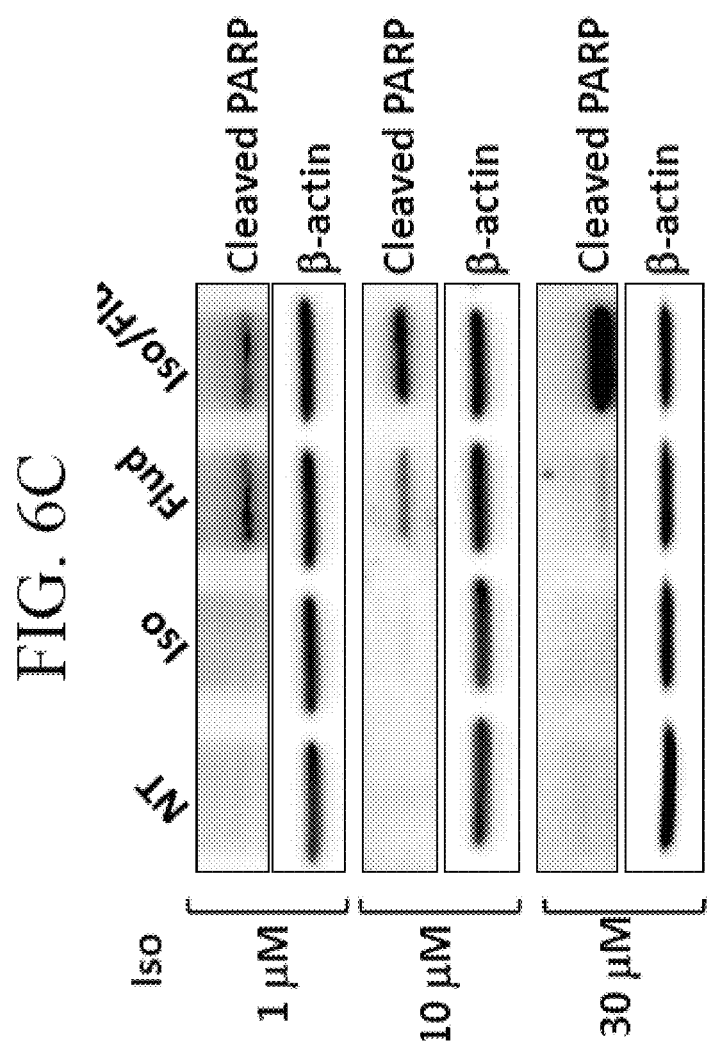

Higher is the concentration of Isoproterenol used, higher was the cytotoxic effect of the combination and lower was the IC50. IC50 values of the different treatments are indicated in (FIG. 6A). (B) The effect of isoproterenol dose-effect on combination efficiency was assessed by western blotting using cleaved PARP as a marker of cell-death, see FIG. 6B. Isoproterenol (30 µM) was also combined with two different anthracyclines (doxorubicin (0.5 µM) and mitoxantrone (0.5 µM)), results showed that these combinations have additive effect no synergistic effect was observed as seen in FIG. 6C.

Control primary CLL cells (NT) and primary CLL cells pre-treated with 30 uM isoproterenol (Iso), 10 uM fludarabine (Flud), a combination of both drugs at these concentrations (Flud/Iso), 0.5 uM doxorubicin (Dodo), a combination of 0.5 uM doxorubicin and 30 uM isoproterenol (Dodo/Iso), 0.5 uM mitoxantrone, and a combination of 0.5 uM mitoxantrone and 30 uM isoproterenol and incubated. Cells were than harvested and examined by immunoblotting with the indicated apoptotic markers. As shown by the appearance of cleaved PARP in FIGS. 6B and 6C and by the relative pixel density in FIG. 6D, fludarabine-induced apoptosis in CLL B cells which was significantly potentiated by isoproterenol.

The in The resulting data indicated that Iso treatment doesn't induce any increase in p53 expression, moreover the amount of P53 induced following fludarabine treatment doesn't increase when fludarabine is combined with Iso. These results show that P53 is not involved in cell death synergistically induced by Iso/fludarabine treatment.

As disclosed herein, the inventors have developed new methods and compositions for enhancing the activity of purine analogs such as fludarabine by increasing the effective concentration of the purine analog compared to intracellular ATP. A reduction of intracellular ATP, for example by an ATP depleting agent such as isoproterenol or LY309887 or Methotrexate e, increases the affinity of the analog for receptors that bind to ATP or to the analog. By reducing the concentration of ATP, the analog can bind more efficiently to intracellular receptors to which ATP binds and exert functional activity, such as an anticancer or cytotoxic activity against cells exposed to both the ATP depleting agent and the purine analog. Essentially, ATP is a competitive inhibitor of the binding of the purine analog to shared intracellular receptors. Reducing the concentration of ATP reduces the competitive inhibition by ATP to the binding of the purine analog to these receptors. Purine analogs may interfere with one or more of the following cellular functions: DNA synthesis, RNA synthesis, decrease intracellular levels of guanine nucleotides, or damage nucleic acids by the incorporation of the purine analog.

This combination of drugs has been shown to be useful for myeloablation or myelosuppression of leukemia cells and the combination to exhibit a more than additive synergistic effect. Due to the increased synergistic activity of the drug combinations disclosed herein, dosages of the anticancer drugs can be reduced and yet still provide equal or superior antineoplastic effects.

Terminology. Terminology used herein is for the purpose of describing particular embodiments only and is not intended to be limiting of the invention.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, these terms are synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim including additive or synergistic effects of combining a purine analog and a drug or agent that depletes ATP. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

As used herein, the term "and/or" includes any and all combinations of one or more of the associated listed items and may be abbreviated as "/".

Links are disabled by spelling out of or deletion of http: or by insertion of a space or underlined space before www. Unless otherwise indicated, the text available via the link on the filing date of the application is incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all subranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

Whenever a range is given in the specification, for example, a temperature range, a time range, or a composition or concentration range, all intermediate ranges and subranges, as well as all individual values included in the ranges given are intended to be individually included in the disclosure. It will be understood that any subranges or individual values in a range or subrange that are included in the description can be optionally excluded from embodiments of the invention.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method for treating a patient with a cancer, comprising:
    administering a purine analog in combination with an adenylate cyclase activator that depletes intracellular ATP of cells of the cancer,
    wherein the purine analog in combination with the adenylate cyclase activator that depletes intracellular ATP exhibits greater cytotoxicity on, or a greater ability to inhibit proliferation of, the cancer cells than either the purine analog by itself or the adenylate cyclase activator that depletes intracellular ATP by itself.

2. The method of claim 1, wherein the purine analog is fludarabine.

3. The method of claim 1, wherein the adenylate cyclase activator that depletes intracellular ATP is isoproterenol (ISO) or another drug that converts ATP into cAMP.

4. The method of claim 1, wherein the purine analog is fludarabine, indacaterol, or bendamustine and the adenylate cyclase activator that depletes intracellular ATP is isoproterenol (ISO).

5. The method of claim 1, wherein the purine analog is fludarabine which is administered in an amount ranging from 5 to 50 mg/m$^2$ and the adenylate cyclase activator that depletes intracellular ATP is isoproterenol which is administered in an amount ranging from 0.02 to 0.06 mg.

6. The method of claim 1, further comprising administering methotrexate.

7. The method of claim 1, wherein the purine analog is fludarabine and which method further comprises administering LY 309887.

8. The method of claim 7, wherein the purine analog is fludarabine which is administered in an amount ranging from 5 to 50 mg/m$^2$ and the LY309887 is administered in an amount ranging from 1 to 50 mg.

9. The method of claim 1, wherein the purine analog is fludarabine which is administered in an amount ranging from 5 to 50 mg/m² and the method further comprises administering methotrexate in an amount ranging from 1 to 50 mg.

10. The method of claim 1, wherein administering does not comprise administering a PDE inhibitor or other anticancer drug.

11. The method of claim 1, wherein the patient has leukemia or lymphoma.

12. The method of claim 1, wherein the patient has chronic lymphocytic leukemia (CLL).

13. The method of claim 1, wherein the patient has chronic myeloid leukemia (CML).

14. The method of claim 1, wherein the patient has acute lymphocytic leukemia (ALL).

15. The method of claim 1, wherein the patient has acute myeloid leukemia (AML).

16. The method of claim 1, wherein the patient has Hairy cell leukemia (HCL).

17. A method for selecting a cancer patient for treatment with a purine analog comprising:

determining whether an adenylate cyclase activator that depletes intracellular ATP in normal cells depletes intracellular ATP in cancer cells from the patient, selecting a patient having cancer cells whose intracellular ATP is depleted by said adenylate cyclase activator, and treating the cancer patient with the adenylate cyclase activator that depletes intracellular ATP and with a purine analog.

18. The method of claim 17, wherein the intracellular ATP is depleted to a level not more than 50% of a corresponding control cancer cell not treated with said adenylate cyclase activator.

19. The method of claim 17, wherein the adenylate cyclase activator that depletes intracellular ATP is isoproterenol and the purine analog is fludarabine.

20. The method of claim 17, wherein said cancer patient has leukemia.

\* \* \* \* \*